United States Patent
Yamamoto et al.

(10) Patent No.: US 10,781,290 B2
(45) Date of Patent: Sep. 22, 2020

(54) MULTIPLE METAL SALT ASSEMBLY OF DENDRIMER HAVING FOUR OR MORE TYPES OF MULTIPLE-METAL SALT COMPOUND PRECISELY ASSEMBLED, AND METHOD FOR PRODUCING SUBNANO METAL PARTICLES

(71) Applicant: TOKYO INSTITUTE OF TECHNOLOGY, Tokyo (JP)

(72) Inventors: Kimihisa Yamamoto, Tokyo (JP); Takamasa Tsukamoto, Tokyo (JP); Tetsuya Kambe, Tokyo (JP); Naoki Haruta, Tokyo (JP); Takane Imaoka, Tokyo (JP)

(73) Assignee: TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 16/489,870

(22) PCT Filed: Feb. 23, 2018

(86) PCT No.: PCT/JP2018/006789
§ 371 (c)(1),
(2) Date: Aug. 29, 2019

(87) PCT Pub. No.: WO2018/159505
PCT Pub. Date: Sep. 7, 2018

(65) Prior Publication Data
US 2019/0382537 A1    Dec. 19, 2019

(30) Foreign Application Priority Data

Mar. 1, 2017 (JP) .................................. 2017-038389
Nov. 29, 2017 (JP) .................................. 2017-228985

(51) Int. Cl.
C08G 83/00    (2006.01)
C08L 101/00    (2006.01)
(Continued)

(52) U.S. Cl.
CPC .......... *C08G 83/004* (2013.01); *C07C 251/24* (2013.01); *C08G 73/026* (2013.01);
(Continued)

(58) Field of Classification Search
CPC .............. C08K 3/013; C08K 2201/011; C08L 101/005; C08G 73/026; C08G 73/00;
(Continued)

(56) References Cited

FOREIGN PATENT DOCUMENTS

| JP | 2007-23166 | 2/2007 |
|----|------------|--------|
| JP | 2010-18610 | 1/2010 |
| JP | 2013-159588 | 8/2013 |

OTHER PUBLICATIONS

Enoki et al. Organic Letters 2006 vol. 8, No. 4.*
(Continued)

*Primary Examiner* — Shane Fang
(74) *Attorney, Agent, or Firm* — Wenderoth, Lind & Ponack, L.L.P.

(57) ABSTRACT

A multiple-metal salt assembly of a dendrimer in which multiple-metal salt compounds with a number of, for example, four or more types of multiple metals can be assembled for each of parts with different environments so that the total metal atom number becomes less than 60. Also, a method for producing the multiple-metal salt assembly, and a method for producing subnano metal particles including the multiple-metal salt assembly of the dendrimer.

20 Claims, 29 Drawing Sheets

(51) Int. Cl.
  *C07C 251/24* (2006.01)
  *C08K 3/013* (2018.01)
  *C08G 73/02* (2006.01)
(52) U.S. Cl.
  CPC .......... *C08K 3/013* (2018.01); *C08L 101/005* (2013.01); *C08K 2201/011* (2013.01)
(58) Field of Classification Search
  CPC ....... C08G 83/004; C07C 251/24; C07F 5/00; C07F 7/22; C07F 7/00; C07F 1/12
  See application file for complete search history.

(56) References Cited

OTHER PUBLICATIONS

International Search Report dated Apr. 24, 2018 in International Application No. PCT/JP2018/006789.
Koizumi et al., "Catalytic Activity of Multi-metallic Subnanoclusters for Oxidation of Alkane", The Chemical Society of Japan 95-th Annual Meeting (Mar. 26 to 29, 2015 at School of Pharmacy, Nhon University, Funabashi campus, school of pharmacy) Presentation No. 3F8-02 Preprints.
Koizumi et al., "Oxidation of Hydrocarbons Catalyzed by Multi-metallic Clusters", The Chemical Society of Japan 96-th Annual Meeting (Mar. 24 to 27, 2016 at Doshisha University, Kyotanabe campus) Presentation No. 2B2-48 Preprints.
Takanashi et al., "Heterometal Assembly in Dendritic Polyphenylazomethines", Bull. Chem. Soc. Jpn. vol. 80, No. 8, pp. 1563-1572 (2007).
Polymer preprints, vol. 55, No. 2, (2006), pp. 3071-3072 (Presentation Nno. 3F14).
Koizumi et al., "Synthesis and catalytic activities of multi-metallic clusters using a dendrimer template", 9th annual meeting of Japan Society for Molecular Science (Sep. 16 to 19, 2015 at Tokyo Institute of Technology, Ookayama campus) Presentation No. 1P079, Abstract.
Extended European Search Report dated Mar. 31, 2020 in corresponding European Patent Application No. 18760784.1.
Yamamoto et al., "Precision Synthesis of Subnanoparticles Using Dendrimers as a Superatom Synthesizer", Accounts of Chemical Research, vol. 47, No. 4, pp. 1127-1136 (2014).

* cited by examiner

MULTIPLE METAL SALT ASSEMBLY OF DENDRIMER HAVING FOUR OR MORE TYPES OF MULTIPLE-METAL SALT COMPOUND PRECISELY ASSEMBLED, AND METHOD FOR PRODUCING SUBNANO METAL PARTICLES

TECHNICAL FIELD

The present invention relates to a multiple-metal salt assembly of dendrimer having multiple-metal salt compound precisely assembled, a method for producing the same, and a method for producing subnano metal particles using the multiple-metal salt assembly of the dendrimer.

BACKGROUND ART

It has been known that the oxidation reaction is the fundamental and primary reaction operation in chemical fields including resource chemistry, fuel chemistry, organic synthetic chemistry, and environmental chemistry. Regarding this oxidation reaction, using various catalysts in either a gas phase reaction or a liquid phase reaction has been attempted and various metal catalysts have been put into practical application. However, in the conventional catalyst oxidation reaction, in the case of using air or oxygen as an oxidant, it is necessary to employ a high-temperature condition or, in the liquid phase reaction, use an organic solvent that has a large burden on the environment; additionally, the catalyst reaction efficiency has not been always high, which is a problem.

In view of the above background, as the catalyst with excellent reactivity, an inhomogeneous catalyst structure that has been made into microparticles, such as microparticles or nanoparticles, has attracted attention and examinations have been advanced from various ways and perspectives. In the case of the microparticles with a size of 10 nm or less, the band gap is large and the particles are dispersive because of the quantum effect, and as the particles are made into the microparticles, the active surface area is increased; therefore, higher activity than a bulk can be expected.

As a method for producing the nanoscale microparticles that can also be used as the catalyst, a method of using phenylazomethine dendrimer as a mold, which is a unique method conceived by the present inventors, has come to be researched and developed extensively. The phenylazomethine dendrimer, which has been developed and examined by the present inventors, includes a number of imine parts exhibiting high coordination to a skeleton, so that a complex can be formed with Lewis acid. The phenylazomethine dendrimer has such an electron density gradient that, as electron donation from imine increases from a terminal to a center, the electron density of imine increases from the imine at the terminal to the center. When a metal salt forms a complex with the phenylazomethine dendrimer, stepwise complexation occurs because of this electron density gradient; specifically, imine in the innermost layer forms complex with the metal salt with priority. By utilizing the stepwise complexation of the phenylazomethine dendrimer, not just single one-dimensional system such as platinum salt but also two-dimensional precision heterometal assembling using two types of metal salts having multiple metal species assembled in the respective layers become possible, and thus, the dendrimer complex with a prescribed number of metal salts with a prescribed composition can be prepared. By reducing the dendrimer complex with this metal salt coordinated thereto, it is possible to form a metal subnano cluster with a particle size distribution precisely controlled to be very small (Patent Literatures 1 to 3).

As a result of extending the aforementioned examinations, the present inventors have successfully formed the complex of novel three types of multiple-metal salts, gold chloride, platinum chloride, and copper chloride, that have never been combined before, assembled stepwise from the inner layer of the phenylazomethine dendrimer (Non Patent Literatures 1, 2).

Regarding the assembling of multiple-metal salt into phenylzomethine dendrimer, the present inventors have examined to assemble the multiple-metal salt to phenylazomethine dendrimer in which complex-forming parts of and after a first generation that are branched from the core into trees are in the same environment and the layers in the respective generations branched into trees are symmetric in the complex formation in Non-Patent Literatures 1 and 2, for example. In Non-Patent Literature 3, by using the phenylazomethine dendrimer with the fourth generation having a benzene ring as a core, $FeCl_3$, $GaCl_3$, $VCl_3$, and $SnCl_2$ are sequentially assembled to the layers in the respective generations so that two are placed in the layer in the first generation, four are placed in the layer in the second generation, eight are placed in the layer in the third generation, and sixteen are placed in the layer in the fourth generation, that is, the number of salts that fill up to the respective layers is 2, 6, 14, and 30. In Non-Patent Literature 4, by using the phenylazomethine dendrimer with the fourth generation having porphyrin as a core, four types of multiple-metal salts are assembled to the layers in the respective generations so that four are placed in the layer in the first generation, eight are placed in the layer in the second generation, sixteen are placed in the layer in the third generation, and thirty-two are placed in the layer in the fourth generation, that is, the number of salts that fill up to the respective layers is 4, 12, 28, and 60. In Non-Patent Literature 5, by using the phenylazomethine dendrimer with the fourth generation having tetraphenylmethane as a core, four types of multiple-metal salts are assembled to the layers in the respective generations so that four are placed in the layer in the first generation, eight are placed in the layer in the second generation, sixteen are placed in the layer in the third generation, and thirty-two are placed in the layer in the fourth generation, that is, the number of salts that fill up to the respective layers is 4, 12, 28, and 60.

CITATION LIST

Patent Literature

Patent Literature 1: JP-A-2010-18610
Patent Literature 2: JP-A-2013-159588
Patent Literature 3: JP-A-2007-23166

Non-Patent Literature

Non-Patent Literature 1: The Chemical Society of Japan 95-th Annual Meeting (Mar. 26 to 29, 2015 at School of Pharmacy, Nihon University, Funabashi campus, school of pharmacy) Presentation No. 3F8-02 Preprints
Non-Patent Literature 2: The Chemical Society of Japan 96-th Annual Meeting (Mar. 24 to 27, 2016 at Doshisha University, Kyotanabe campus) Presentation. No. 2B2-48 Preprints
Non-Patent Literature 3: Bull. Chem. Soc. Jpn, Vol. 80 No. 8 1563-1572 (2007).

Non-Patent Literature 4: Polymer preprints, Vol. 55 No. 2 (2006), 3071-3072 (Presentation No. 3F14)

Non-Patent Literature 5: 9th annual meeting of Japan Society for Molecular Science (Sep. 16 to 19, 2015 at Tokyo Institute of Technology, Ookayama campus) Presentation No. 1P079, Abstract

SUMMARY OF INVENTION

Technical Problem

However, the stepwise assembling by more than four types of multiple metals has been impossible in the technique in which the phenylazomethine dendrimer with the fourth generation is used. In the examinations that have been conducted so far, the phenylazomethine dendrimer with the fourth generation including 60 imine parts in one molecule is the main symmetry. Using phenylazomethine dendrimer having five or more generations in order to assemble five or more types of multiple-metal salts results in the restriction because more tree branches are generated. In addition, if the number of metal atoms exceeds 60, the advantage of subnano particles may be lost. In view of this, a technique that enables the stepwise assembling of four, or five or more types of multiple metals, which has never been realized before, with as few metal atoms in total as possible has been expected.

Even if stepwise assembling by four or more types of multiple metals is enabled, it is assumed that a number of, specifically four or more types, particularly five or more types of multiple-metal complexes are precisely assembled stepwise with the number of complexes prescribed, unpredictable factors that cannot be covered from the theoretical aspects may occur complicatedly, such as the increase in complexation constants to the complex forming parts with the different complexation strength in the dendrimer, counter anion substitution possibility, and the resulting change in complexation strength, all of which need to be considered for each multiple-metal salt. It is difficult to exactly predict whether the stepwise precise assembling can be achieved or the assembling becomes non-stepwise and random. The theoretical foreknowledge to be the guideline of the stepwise assembling and the non-stepwise assembling, in which two types of multiple-metal complexes are the model, has been attempted; however, the accurate theoretical prediction in the model involving a number of multiple-metal complexes such as four or more types of multiple-metal complexes has not been achieved and experimental results have not been obtained yet. That is to say, the precise assembling with four or more types of multiple-metal complexes has not been clarified yet, particularly in the case where the core is changed from the conventional one.

The present invention has been made in view of the above circumstances, and it is an object of the present invention to provide a multiple-metal salt assembly of dendrimer in which multiple-metal salt compound including a number of, specifically four or more, particularly five or more types of multiple-metals can be precisely assembled for each of parts with different environments so that, particularly, the total metal atom number becomes less than 60, a method for producing the same, and a method for producing subnano metal particles using the multiple-metal salt assembly of dendrimer.

Solution to Problem

As a result of earnest researches for solving the above problem, the present inventors have found out that: by introducing a part to which metal salt can be coordinated by replacing a part of four phenylene groups of tetraphenylmethane as the core, the metal salt forms the complex at the core part first, and the complex forming part of that part in each layer of, and after the first generation has the environment different from that of another complex forming part, and thus, for example, the metal salts can be assembled to the layers in the respective generations in manner that one is placed in the core, one and three are placed in the layer in the first generation, two and six are placed in the layer in the second generation, four and twelve are placed in the layer in the third generation, and eight and twenty-four are placed in the layer in the fourth generation, that is, the number of metal salts that fill up to the respective layers is 1, 2, 5, 7, 13, 17, 29, and 37. Therefore, a number of, specifically four or more, additionally five or more multiple-metal salts, which has never been achieved before, can be assembled so that the total metal atom number becomes less than 60. Accordingly, the present invention has been completed.

As a solution to the problem, the present invention provides a multiple-metal salt assembly of dendrimer, in which four or more types of multiple-metal salt compounds with multiple metal species are assembled for each of parts with different environments in dendrimer whose core is a group expressed by the following Formula (I):

[Chem. 1]

$$—(X)_nC(Ph)_{4-n}— \tag{I}$$

(In the formula, n number of Xs independently represent a divalent group corresponding to a residue of a six-membered ring aromatic heterocyclic compound including, as a hetero atom, at least one selected from nitrogen, phosphorus, and arsenic, a derivative thereof, or a benzene derivative including an electron-donating functional group, Ph represents a phenylene group, and n represents an integer of 1 to 3.)

A method for producing subnano metal particles according to the present invention is a method for producing subnano metal particles including four or more types of multiple-metals, in which the dendrimer complex is reduced.

A method for producing a dendrimer complex according to the present invention is a method for producing a multiple-metal salt assembly of dendrimer in which four or more types of multiple-metal salt compounds with multiple metal species are assembled for each of parts with different environments, the method including the steps of:

preparing a solution containing dendrimer whose core is a group expressed by the following Formula (I):

[Chem. 2]

$$—(X)_nC(Ph)_{4-n}— \tag{I}$$

(in which n number of Xs independently represent a divalent group corresponding to a residue of a six-membered ring aromatic heterocyclic compound including, as a hetero atom, at least one selected from nitrogen, phosphorus, and arsenic, a derivative thereof, or a benzene derivative including an electron-donating functional group, Ph represents a phenylene group, and n represents an integer of 1 to 3); and mixing the solution with the four or more types of multiple-metal salt compounds with different interaction strength for each of the parts with the different environments in the dendrimer, so as to obtain the multiple-metal salt assembly of dendrimer in which the four or more types of multiple-metal salt compounds are assembled for each of the parts with the different environments.

Advantageous Effects of Invention

According to the present invention, a multiple-metal salt assembly of dendrimer in which multiple-metal salt compounds of a number of, specifically four or more, particularly five or more types of multiple-metals can be precisely assembled for each of parts with different environments so that particularly, the total metal atom number becomes less than 60, and a method for producing the same, and a method for producing subnano metal particles including the multiple-metal salt assembly of the dendrimer are provided.

DESCRIPTION OF EMBODIMENTS

Figure 1:
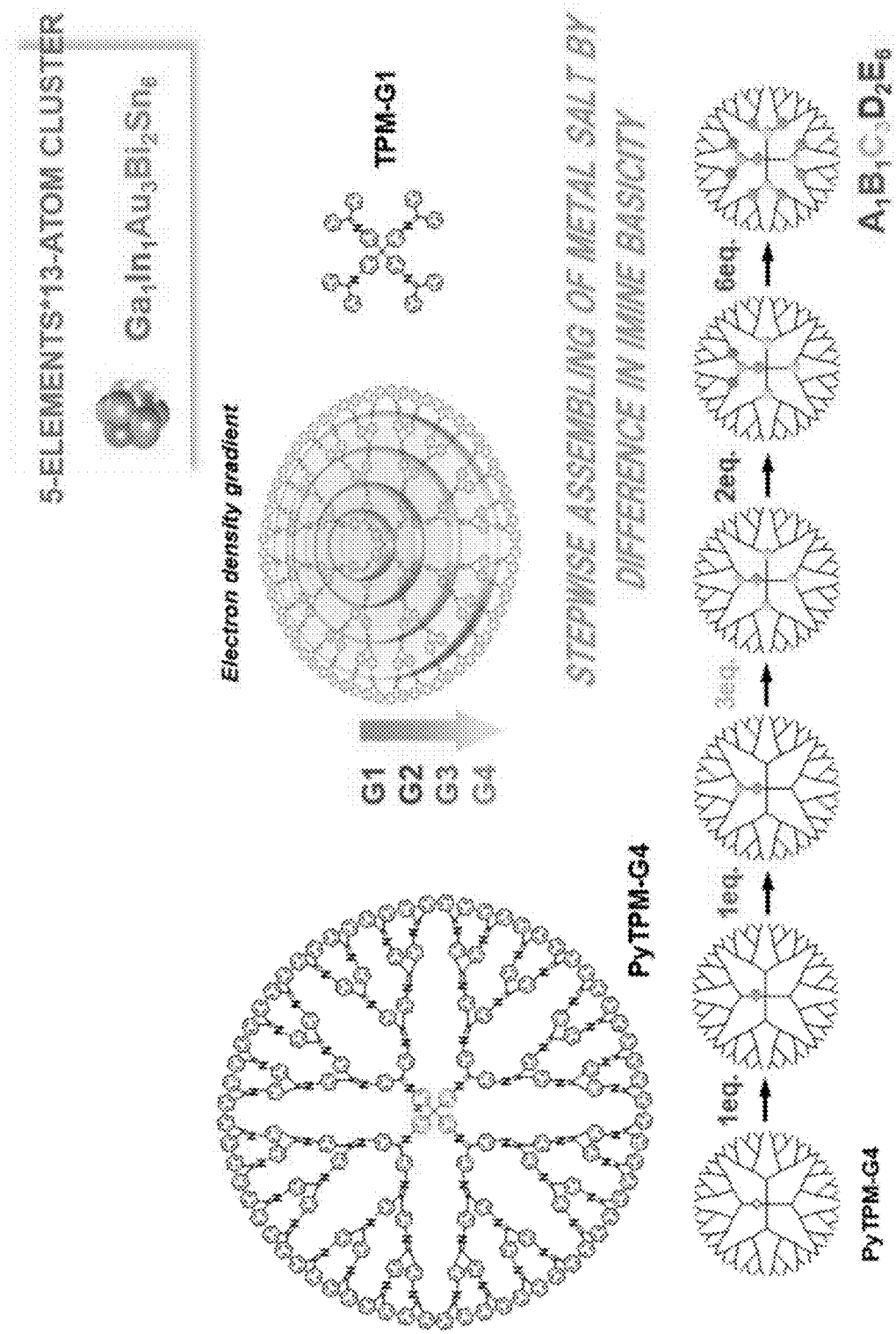
FIG. 1 is a conceptual diagram for describing stepwise assembling of 5 elements 13 atoms to phenylazomethine dendrimer in Example 1.

The present invention is hereinafter described in detail.

In the present invention, "parts with different environments" of dendrimer refers to parts in which metal salts can be assembled in the dendrimer and the interaction with the metal salt compound is different in these parts. The parts include a complex forming part, an ionic bond part, and a covalent bond part with the metal salt compound. "Complex forming part" refers to the part that forms the complex with the metal salt compound in the dendrimer and that serves as a Shiff base. In the unidirectional electron density gradient dendrimer, the strength of the interaction such as the complexation strength changes stepwise so as to decrease gradually from the inner layer to the outer layer; thus, the parts with different environments are formed. In addition to that, in the case where the dendrimer having an electron-donating ligand in the outermost layer has the strong coordinate environment only in the outermost layer, the parts with the different environments are formed so that the part with the most intensive interaction becomes the outermost layer and the interaction in the inner layer becomes lower than that.

In the present invention, "the strength of interaction" means how easily the complex, the ionic bond part, the covalent bond, or the like is formed between the dendrimer and the metal salt compound; "the complexation strength" of the dendrimer means the basicity as the Shiff base to the assembled metal salt compound is high and the electron density is high. "The complexation strength" of the multiple-metal salt compound means the strength as the Lewis acid that is assembled in the complex forming part with the basicity of the dendrimer. This complexation strength can be determined relatively from the result of plotting the absorbance at the wavelength where the absorption increases as the complex is formed, with respect to the density ratio (metal salt/dendrimer) by the ultraviolet-visible absorption spectrum when the metal salt is dripped in the solution of the dendrimer.

In the present invention, "the metal salt compound" widely covers the salt of metal and anion, the complex with the ligand, and the like; furthermore, the metal salt that is coordinated directly to the part of the dendrimer with the different environment, and the compound in which a proton or an organic cation having the metal salt as the counter anion is coordinated to that part are also covered. In the present invention, in the dendrimer, the multiple-metal salt may be coordinated directly to the part with the different environment, or the proton or the organic cation having the multiple-metal salt as the counter anion may be coordinated to be assembled. In this case, "the interaction with the metal salt" can be replaced by "interaction with organic cation or proton".

The multiple-metal salt assembly of the dendrimer according to the present invention is formed by assembling four or more types of multiple-metal salt compounds with multiple metal species, for each part with different environment of the dendrimer whose core is the group expressed by the above Formula (I).

In Formula (I), n number of Xs independently represent a divalent group corresponding to a residue of a six-membered ring aromatic heterocyclic compound or a derivative thereof, or a benzene derivative including an electron-donating functional group, Ph represents a phenylene group, and n represents an integer of 1 to 3.

The multiple-metal salt assembly according to the present invention also includes the part with the different environment in the core itself. In the unidirectional electron density gradient dendrimer, the basicity gradient is observed from the core to the terminal; therefore, the complexation constant of the complex forming part in the core or in the first generation that is closest to the core is the highest, and the complexation constant decreases gradually to the outside. By using the difference in complexation constant as the driving power, the metal salt compounds are assembled stepwise starting from the core or the generation closest to the center, in the order of the first, second, and third generations.

Figure 25:
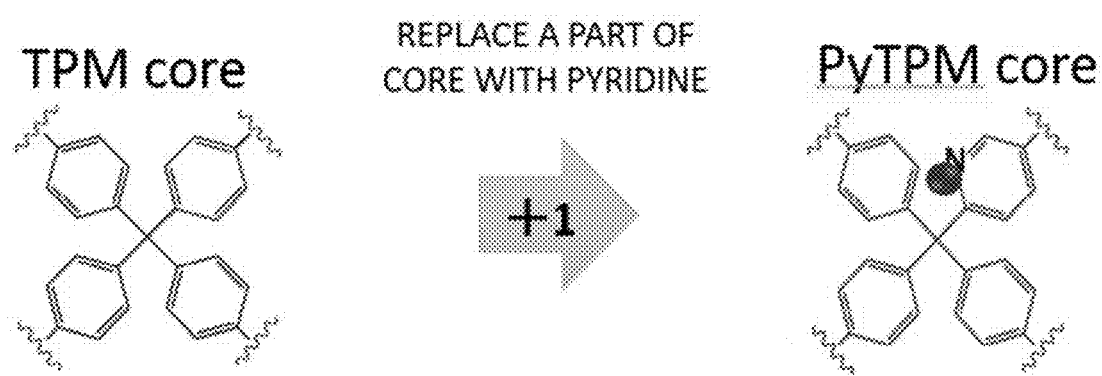
FIG. 25 is a conceptual diagram showing the change of a coordinating site when the core of dendrimer is changed from triphenyl methane (TPM) to pyridine (PyTPM).
Figure 26:
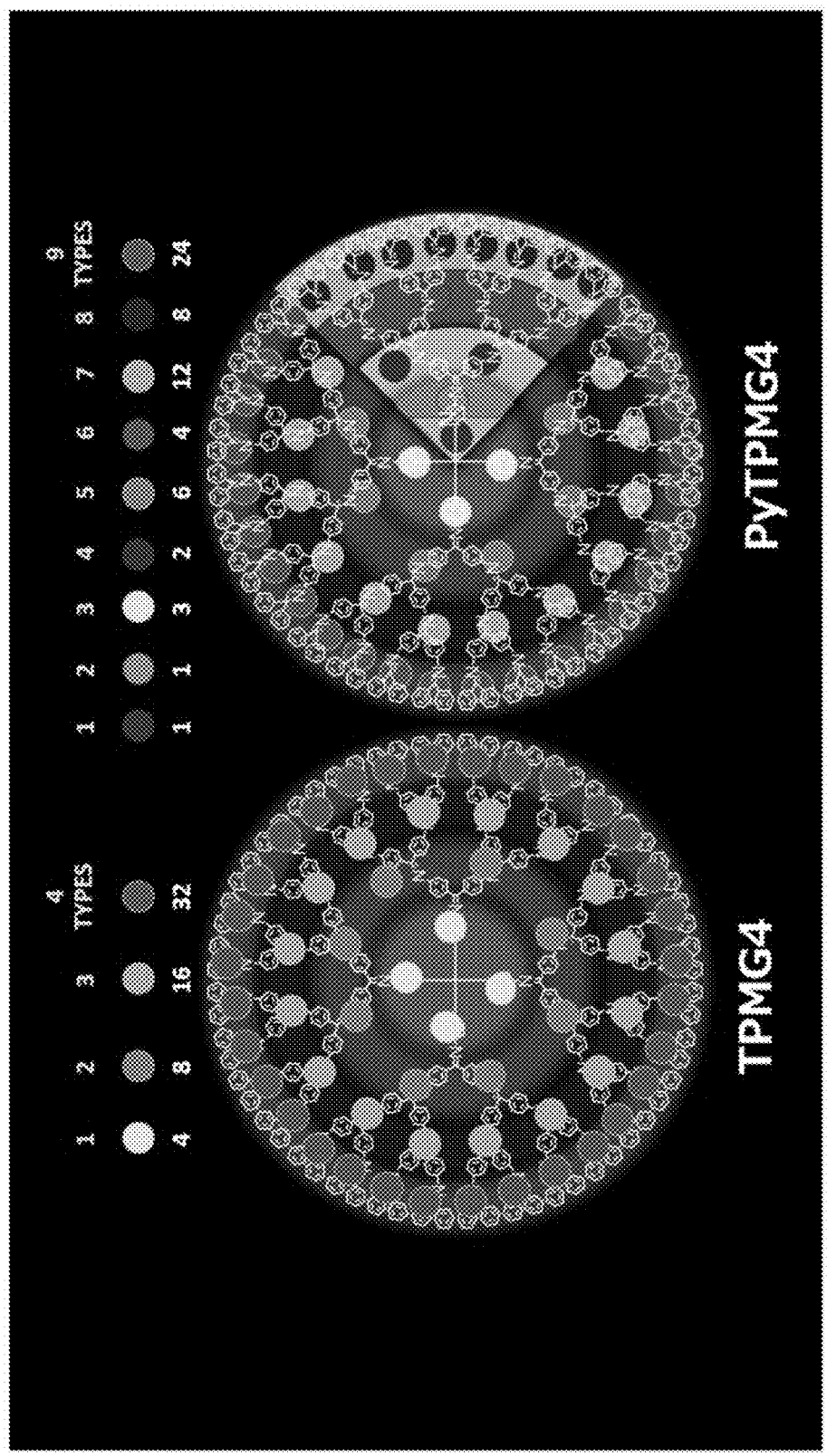
FIG. 26 is a conceptual diagram showing the assembly of D4 dendrimer to the multiple-metal salt when the core of dendrimer is changed from triphenyl methane (TPM) to pyridine (PyTPM).

The number of metal salts that fill up to the respective layers is, in the case where the number of branches of the core is 4 like tetraphenylmethane, 4, 12, 28, and 60; in the case where the number of branches of the core is 3, the number is 3, 9, 21, and 45; and in the case where the number of branches of the core is 2, the number is 2, 6, 14, and 30. In the dendrimer (FIG. 25) like pyridyltriphenylmethane core in which one coordinate site is added to the core as in the present invention, the complex forming part in a part of each layer in and after the first generation is in the environment different from the environment of another complex forming part. Thus, the number of metal salts that fill up to the respective layers is one in the core, one and three in the layer in the first generation, two and six in the layer in the second generation, four and twelve in the layer in the third generation, and eight and twenty four in the layer in the fourth generation, that is, the number of metal salts that fill up to the respective layers is 1, 2, 5, 7, 13, 17 29, and 37 (FIG. 26). That is to say, the complex is formed with the complex forming part (imine part) of the dendron that is bonded to the pyridine part of pyridyltriphenylmethane core first, and then, the complex is formed with another complex forming part in each layer.

In Formula (I), the above description applies when n is equal to 1; if n is equal to 2, for example, the assembling to the layers in the respective generations is possible so that two in the core, two and two in the layer in the first generation, four and four in the layer in the second generation, eight and eight in the layer in the third generation, and sixteen and sixteen in the layer in the fourth generation, that is, the number of metal salts that fill up to the respective layers is 2, 4, 6, 10, 14, 22, 30, and 46 including the core. If n is equal to 3, the assembling to the layers in the respective generations is possible so that, for example, three in the core, three and one in the layer in the first generation, six and two in the layer in the second generation, twelve and four in the layer in the third generation, and twenty-four and eight in the layer in the fourth generation, that is, the number of metal salts that fill up to the respective layers is 3, 6, 7, 13, 15, 27, 31, and 55 including the core.

That is to say, in each layer in and after the first generation, two or more parts with different environments are formed; therefore, at least eight parts with different environments in 60 or less assembling sites can be formed.

Therefore, stepwise assembling of five or more types of multiple-metal salt compounds becomes possible and particularly, the assembling with fewer total atom number becomes possible; accordingly, the application range of subnano particles expands drastically.

In Formula (I), the six-membered ring aromatic heterocyclic compound includes at least one type selected from nitrogen, phosphorus, and arsenic as a hetero atom. Among these elements, nitrogen is preferable.

Examples of the six-membered ring aromatic heterocyclic compound including nitrogen as the hetero atom include pyridine, pyridazine, pyrimidine, pyradine, and 1,2,3-triazine.

Examples of the six-membered ring aromatic heterocyclic compound including phosphorus as the hetero atom include phosphorine.

Examples of the six-membered ring aromatic heterocyclic compound including arsenic as the hetero atom include arsenine.

Examples of the derivative of the six-membered ring aromatic heterocyclic compound include the six-membered ring aromatic heterocycle with a hydrogen atom substituted by a monovalent group, or the derivative that forms a condensed ring with two adjacent atoms in the six-membered ring aromatic heterocycle.

Examples of the substituent of the derivative of the six-membered ring aromatic heterocyclic compound include halogen atoms (such as fluorine atom, chlorine atom, bromine atom, and iodine atoms), alkyl groups with 1 to 6 carbon atoms (such as methyl and ethyl), aryl groups (aryl groups with 6 to 20 carbon atoms, such as phenyl and naphthyl), cyano groups, carboxyl groups, alkoxycarbonyl groups (such as methoxy carbonyl), aryloxycarbonyl groups (such as phenoxycarbonyl), substituted or unsubstituted carbamoyl groups (such as carbamoyl, N-phenylcarbamoyl, N,N-dimethylcarbamoyl), alkylcarbonyl groups (such as acetyl), arylcarbonyl groups (such as benzoyl), nitro groups, substituted or unsubstituted amino groups (such as amino, dimethylamino, anilino), acylamino groups (such as acetoamide and ethoxycarbonylamino), sulfonamide groups (such as methane sulfonamide), imide groups (such as succinimide and phthalimide), imine groups (such as benzylideneamino), hydroxy groups, alkoxy groups with 1 to 6 carbon atoms (such as methoxy), aryloxy groups (such as phenoxy), acyloxy groups (such as acetoxy), alkyl sulfonyl oxy groups (such as methane sulfonyl oxy), aryl sulfonyl oxy groups (such as benzene sulfonyl oxy), sulfo groups, substituted or unsubstituted sulfamoyl groups (such as sulfamoyl, N-phenylsulfamoyl), alkylthio groups (such as methylthio), arylthio groups (such as phenylthio), alkylsulfonyl groups (such as methane sulfonyl), arylsulfonyl groups (such as benzene sulfonyl), and aromatic heterocyclic groups (such as 4 to 20 carbon atoms).

The derivative that forms the condensed ring with the adjacent carbon atoms in the six-membered ring aromatic heterocycle is, for example, the derivative in which the ring to be added to the six-membered ring aromatic heterocycle is the aryl group (for example, 6 to 20 carbon atoms), the heterocyclic group (for example, 4 to 20 carbon atoms), or the like.

Among these, the six-membered ring aromatic heterocyclic compound and its derivative are preferably pyridine.

Regarding the divalent groups corresponding to the residues of the six-membered ring aromatic heterocyclic compound and the derivative thereof, the position of the two bonding parts is not limited to a particular position; however, the bonding position is preferably para-positions of the six-membered ring aromatic heterocycle, particularly, the carbon atom position.

Examples of the benzene derivative including the electron-donating functional group include a benzene ring with a hydrogen atom substituted by a monovalent group including the electron-donating functional group and a derivative that forms a condensed ring including the electron-donating functional group together with two adjacent atoms in the benzene ring. The electron-donating property means having a coordinating property that enables the interaction with the multiple-metal salt, or the proton or the organic cation having the multiple-metal salt as a counter anion and the assembling therewith.

Examples of the electron-donating functional group include a group including a nitrogen atom, a group including an oxygen atom, and a group including a sulfur atom.

Examples of the group including a nitrogen atom include an amino group, a substituted amino group (dialkylamino group), an imino group (—NH—), an amide group, a cyano group, a nitro group, and a nitrogen ring group (nitrogen ring group such as five-membered ring, carbazole group, morpholinyl group).

Examples of the group including an oxygen atom include a hydroxyl group, an ether group, a carboxyl group, an alkoxy group (for example, alkoxy groups with 1 to 6 carbon atoms, such as methoxy group, ethoxy group, propoxy group, and butoxy group), a formyl group, a carbonyl group (—CO—), an ester group (—COO—), and an oxygen ring group (for example, oxygen ring group such as five-membered ring).

Examples of the group including a sulfur atom include a thio group (—S—), a thiol group (—SH), a thiocarbonyl group (—SO—), an alkylthio group ($C_{1-4}$ alkylthio group such as methylthio group and ethylthio group), a sulfo group, a sulfamoyl group, and a sulfinyl group (—$SO_2$—).

The derivative that forms the condensed ring including the electron-donating functional group together with the two adjacent atoms in the benzene ring may be, for example, the derivative in which the ring added to the six-membered ring aromatic heterocycle is the aromatic heterocyclic group (for example, 4 to 20 carbons). Specific examples include quinoline, isoquinoline, quinazoline, phthalazine, quinoxaline, cinnoline, indole, isoindole, benzoimidazole, and benzotriazole.

The benzene derivative including the electron-donating functional group may have a substituent that is shown as an example of the substituent of the derivative of the six-membered ring aromatic heterocyclic compound in addition to the electron-donating functional group described above as the example.

Among these, the benzene derivative including the electron-donating functional group is preferably a substituted amino group.

Regarding the divalent group corresponding to the residue of the benzene derivative including the electron-donating functional group, the position of the two bonding parts is not limited to a particular position; however, the bonding position is preferably para-positions of the benzene ring.

The dendrimer is a tree-form polymer having a structure that is branched regularly from the center, with a central part serving as a core and dendron serving as a side-chain part. The number of times of branching in the dendron part is also referred to as generation. The part that is branched by one step from the central molecule of the dendrimer is referred to as a first generation, and the part that is branched by two steps is referred to as a second generation. In general, the dendrimer is the polymer that is perfectly branched into trees regularly from the core, and has the spherical structure that is sparse near the center and dense near the surface; the number of generations increases as branching is repeated from the center.

The dendrimer can be produced by a divergent method, a convergent method, or the like. A divergent method is a method in which the molecule having a plurality of functional groups is the core and the branches are extended from the center to the outside. A convergent method is a method in which the branches are extended from the outside to the inside, and the branches are attached to the core in the end, thereby forming spherical polymer; the synthesis of the dendron is advanced from the part serving as the outer shell of the dendrimer to the inside and finally, some dendrons are bonded to the core.

The dendrimer in the present invention preferably includes the electron-donating bond or atom as the complex forming part at the branched point of the tree structure. For example, the dendrimer including the nitrogen atom or the oxygen atom having a lone electron pair serving as the electron donator is given. The nitrogen atom to which the metal salt compound can be coordinated may be a nitrogen atom in an azomethine bond (—CH=N—). In the dendrimer in the present invention, the complex forming part preferably includes the imine part.

Examples of the dendrimer used in the present invention include phenylazomethine dendrimer, polyamide amine dendrimer, polyalkylene imine dendrimer such as polypropylene imine dendrimer, polyaryl alkyl ether dendrimer such as polybenzyl ether dendrimer.

Among these, phenylazomethine dendrimer is preferable. Phenylazomethine dendrimer has a rigid structure by π conjugation and is therefore featured in high hardness. Inside the molecule, phenylazomethine dendrimer has a sufficiently wide space and includes a number of coordinating sites that form the complex with the metal salt compound, and is therefore suitable for precise assembling of a number of, specifically, four or more types of multiple-metal salt compounds in the complex forming parts in each step from the inner layer to the outer layer.

Phenylazomethine dendrimer is, for example, a compound expressed by Formula (1) below.

[Chem. 3]

$$AB_pR_q \quad (1)$$

In Formula (1), A represents a core molecule group serving as the core of phenylazomethine dendrimer, and the phenylazomethine dendrimer molecule makes the chain of the unit expressed by B in Formula (1) grow to the outside using this core molecule group as the center. As a result, the grown phenylazomethine dendrimer molecule has a structure in which the Bs have been chained and grown radially with the A serving as the center. The number of times of B chains is referred to as "generation", and the number of generations increases to the outside assuming that the generation adjacent to the core molecule group A is the first generation. A in Formula (1) is expressed by the following formula:

    [Chem. 4]

$R^1$ is the group expressed by the above Formula (I).

B in Formula (1) is expressed by a structure of the following formula in which one azomethine is bonded to the A:

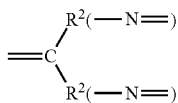    [Chem. 5]

$R^2$ is the aromatic group that may have either the same or different substituent. B forms the generation of phenylazomethine dendrimer and B that is directly bonded to the core molecule group A is the first generation.

R in the above general formula (1) is expressed by the following formula in which azomethine is bonded to the B as a terminating group:

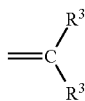    [Chem. 6]

$R^3$ is the aromatic group that may have either the same or different substituent. R is positioned at a terminal of a structure that is extended radially in the phenylazomethine dendrimer molecule.

In Formula (1), p represents the number of generations through the structure of B in the phenylazomethine dendrimer, q represents the number of terminating groups R in the phenylazomethine dendrimer, and $q=2^p \times 4$ is satisfied.

The aromatic group that may have a substituent, $R^2$ and $R^3$, may be independently a phenyl group or its similar structure as a skeleton structure, and examples thereof include a phenyl group, a phenylene group, a biphenyl group, a biphenylene group, a biphenyl alkylene group, a biphenyl oxy group, a biphenyl carbonyl group, and a phenylalkyl group. Examples of the substituent of the skeleton include halogen atoms such as a chlorine atom, a bromine atom, and a fluorine atom, alkyl groups such as a methyl group and an ethyl group, haloalkyl group such as a chloromethyl group and a trifluoromethyl group, alkoxy groups such as a methoxy group and an ethoxy group, alkoxy alkyl groups such as a methoxyethyl group, an alkyl thio group, a carbonyl group, a cyano group, an amino group, and a nitro group. The skeleton may have one or a plurality of substituents as described above.

The phenylazomethine dendrimer expressed by the above Formula (1) is a relatively large molecule as a unimolecular compound (for example, phenylazomethine dendrimer with four generations (n=3) has a diameter of approximately 2 nm), and in the molecule, includes nitrogen atoms at predetermined intervals where the metal atoms can be coordinated. Therefore, phenylazomethine dendrimer can have metal elements one by one regularly inside the molecule that is relatively large as the unimolecular compound.

The size of the phenylazomethine dendrimer can be adjusted as appropriate by selecting the number of generations, the size of the aromatic group bonded to the terminal, or the size of the substituent of the aromatic group bonded to the terminal. By adjusting the size of the phenylazomethine dendrimer on the basis of the structure, the size of the multiple-metal salt assembly of the dendrimer formed using phenylazomethine dendrimer can be adjusted.

In the method for producing the multiple-metal salt assembly of the dendrimer according to the present invention, a solution containing dendrimer is prepared in a first step.

In the present invention, the solvent that dissolves the dendrimer and the multiple-metal salt assembly is not limited to a particular solvent and may be any solvent that can dissolve these. Examples thereof include chlorine containing organic solvent such as dichloromethane, chloroform, 1,2-dichloroethane, 1,1-dichloroethane, and carbon tetrachloride, aromatic organic solvent such as benzene, toluene, xylene, chlorobenzene, anisole, and acetophenone, and cyclohexanone, tetrahydrofurane, limonene, propylene glycol monoethyl ether acetate, and acetonitrile. Two or more types thereof may be used in combination.

The concentration of the dendrimer in the solution before the metal salt compound is mixed is not limited to a particular value; for example, the concentration is preferably 0.001 to 100 µmol/L, more preferably 0.01 to 10 µmol/L.

In the method for producing the multiple-metal salt assembly of the dendrimer according to the present invention, in the next step, four or more types of multiple-metal salt compounds whose strength of interaction is different from each other for each of the parts with different environments in the dendrimer are mixed with the solution, so that the multiple-metal salt assembly of the dendrimer having the four or more types of multiple-metal salt compounds assembled for each of the parts with the different environments is obtained.

The metal element in the four or more types of multiple-metal salt compounds to be assembled in the dendrimer is not limited to a particular metal. This metal element is selected as appropriate in accordance with the purpose of using the metal element, such as the use as the catalyst. Typical examples of the metal element in the multiple-metal salt to be assembled in the dendrimer include titanium, vanadium, iron, cobalt, nickel, copper, zinc, gallium, zirconium, niobium, molybdenum, ruthenium, rhodium, palladium, silver, indium, tin, antimony, hafnium, tantalum, tungsten, osmium, iridium, platinum, gold, and bismuth.

The ligand or the counter anion in the four or more types of multiple-metal salt compounds is not limited to the particular one, and examples thereof include halogen ions such as chloride ions, bromide ions, and iodide ions, trifluoromethane sulfonic acid, acetic acid, acetyl acetone, salen, and cyclopentadiene.

The multiple-metal salt compound may be a multiple-metal salt that is directly coordinated to the part with different environment in the dendrimer, or may be a compound in which the proton or the organic cation having the multiple-metal salt as the counter anion is coordinated to that part and assembled.

Examples of the compound including the multiple-metal salt anion and the organic cation include pentachlorostannate and hexachloroantimonate of phenylmethylium cation.

Examples of the compound including the multiple-metal salt anion and proton include tetrachloroaurate, hexachloroplatinate, hexachloroiridate, hexachloroosmate, perhenate, and tungstate.

The coordination trend of the metal salt can be adjusted by the metal assembling using the electronic effect of the counter anion, the stereoscopic effect of the ligand of the organic ligand, or the dummy coordination trend, that is, the assembling of the metal as the counter anion by the coordination trend of not the metal salt alone but the organic cation or the proton, or by changing the oxidation number of the metal salt. By these means, the coordination trend in the metal assembling can be varied more even with the same element, and two types of metals can be assembled in the different order.

A method of mixing four or more types of multiple-metal salt compounds with the dendrimer solution is not limited to a particular method; for example, the dripping of the solution containing the metal salt compound in the dendrimer solution is given.

As the dendrimer and the metal salt are mixed, in the case of using the complexation of these as an example, the metal element is coordinated to the complex forming part of the dendrimer and is taken into the dendrimer. In the unidirectional electron density gradient dendrimer, here, the metal element is coordinated to the complex forming part on the central side of the dendrimer with priority; therefore, the metal element is coordinated in the order from the complex forming part existing on the central side to the complex forming part on the outside. The metal salt that is mixed first is coordinated from the core of the dendrimer or the complex forming part in the first generation to the outside in accordance with the generation order; then, another metal salt with the low complexation strength, which is mixed next, is coordinated on the outside of the complex forming part to which the previous metal salt has been coordinated. Therefore, by controlling the molar ratio between the dendrimer and the metal salt, the metal element can be arranged at the desired position in the dendrimer.

In the method of assembling the metal salt compound to the dendrimer, the order of dripping the metal salt compound solution and the mixing of the metal solution are not limited. This is because the complexation with the dendrimer part is reversible and the arrangement becomes the most stable in terms of energy. This means the metal with high complex bonding strength is coordinated to the complex forming part with the high coordination trend and the metal with low complex bonding strength is coordinated to the complex forming part with the low coordination trend. In fact, there has been a report that, if the metal with the low complexation strength is assembled in the inner layer with the high coordination trend and then, the metal with the high complexation strength is set, the bonding part is replaced (Bull. Chem. Soc. Jpn. 2007, 80, 1563-1572).

In the present invention, the multiple-metal salt assembly of the dendrimer having the four or more types of multiple-metal salt compounds with multiple metal species assembled for each of the parts with different environments in the dendrimer is obtained. The metal species and the number of metal salt compounds to be assembled here are not limited in particular. In the case of phenylazomethine dendrimer, for example, four to eight types of multiple-metal salt compounds can be assembled; for example, 13 of four types of multiple-metal salt compounds, 13 of five types of multiple-metal salt compounds, 17 of six types of multiple-metal salt compounds, and 37 of eight types of multiple-metal salt compounds can be assembled.

In the method for producing the multiple-metal salt assembly of the dendrimer according to the present invention, the respective multiple-metal salt compounds are preferably mixed by the amount corresponding to the equivalent for one of the parts with different environments where the compounds are assembled or the total equivalent for two or more parts with different environments were the compounds are assembled. After one type of multiple-metal salt compound is mixed, another multiple-metal salt compound is mixed; in this case, it is preferable to cause a change of an isosbestic point in an ultraviolet-visible absorption spectrum of the solution. This aspect is suitable for obtaining the multiple-metal salt assembly of the dendrimer having four or more types of multiple-metal salt compounds assembled for each of the parts with the different environments. That is to say, the complexation between the dendrimer and these metal salt compounds can be performed by controlling the equivalent of the metal salt compounds to the complex forming part of the dendrimer in each generation in the solvent. After the stepwise shift of the isosbestic point is confirmed by the ultraviolet visible absorption spectrum, the next type of metal salt compound is mixed, so that the stepwise assembling is possible. In the case of phenylazomethine dendrimer, as the metal salt compound is mixed, the absorption because of free base imine around 320 nm decreases and the absorption because of the complex near 400 nm increases; thus, it is confirmed that the metal salt is coordinated to the imine part of the dendrimer. As the number of equivalents of the metal salt compound required to change the isosbestic point coincides with the number of imines in each layer, it can be confirmed that the complexation of the metal salt compound occurs stepwise from the inner layer to the outer layer.

In the present invention, it is preferable that when four or more types of multiple-metal salt compounds are mixed in the solution containing the dendrimer, the compounds are assembled to each of the parts with the different environments in the same order. The condition of selecting four or more types of multiple-metal salt compounds that is considered is: the metal salt compounds can be precisely assembled to the dendrimer under the same solvent condition; the metal salt compounds have the different complexation constants under the same solvent condition; and the isosbestic points with the number in accordance with the step of the complex forming parts appear when the dendrimer is mixed and assembled. The condition suitable for obtaining the multiple-metal salt assembly of the dendrimer having four or more types of multiple-metal salt compounds assembled for each of the parts with the different environments is: when four or more types of multiple-metal salt compounds are mixed in the solution containing the dendrimer, the compounds are assembled to each of the parts with the different environments in the same order; for example, when any of the four or more types of multiple-metal salt compounds is mixed alone in the solution containing the dendrimer, the complexation occurs in the order from the inner layer to the outer layer for each complex forming part in each step.

In the mixing and assembling of the metal salts with different complexation constants in the dendrimer, the theoretical consideration as below is taken into consideration.

As shown schematically below, in the assembling of the metal salt to the complex forming part (hereinafter, imine for example) in the dendrimer, a model of using two types of metal salts: strong metal salt and weak metal salt is considered.

Figure 27:
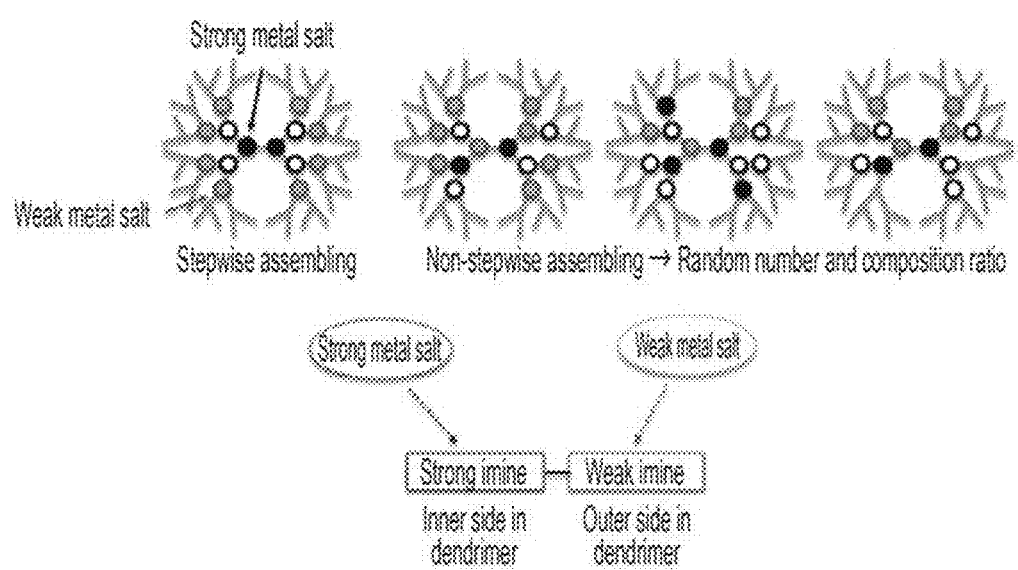
FIG. 27 is a pictorial representation of [Chem. 7].

[Chem. 7]—shown in FIG. 27.

In this manner, the metal salts are stepwise assembled from the strong metal salt to the weak metal salt in the order from the inner strong imine to the outer weak imine or the metal salts are assembled non-stepwise with the random number and the random composition ratio. Regarding the condition and the degree of selectivity when the strong metal salt is assembled on the inside and the weak metal salt is assembled on the outside, assuming the complexation constant between the strong metal salt and the inner strong imine is $K_1$, the complexation constant between the strong metal salt and the outer weak imine is $K_1'$, the complexation constant between the weak metal salt and the inner strong imine is $K_2$, and the complexation constant between the weak metal salt and the outer weak imine is $K_2'$, then a mixed complex A in which the complex is formed by the strong metal salt and the inner strong imine, and the weak metal salt and the outer weak imine, and a mixed complex B in which the complex is formed by the weak metal salt and the inner strong imine, and the strong metal salt and the outer weak imine satisfy the following expression:

$$\frac{\text{Density of mixed complex } A}{\text{Density of mixed complex } B} = \frac{K_1 \times K_2'}{K_2 \times K_1'} = R \qquad \text{[Expression 1]}$$

The selectivity in the stepwise assembling is as below:

$$\frac{R}{R+1} \times 100\% \qquad \text{[Expression 2]}$$

Figure 28:
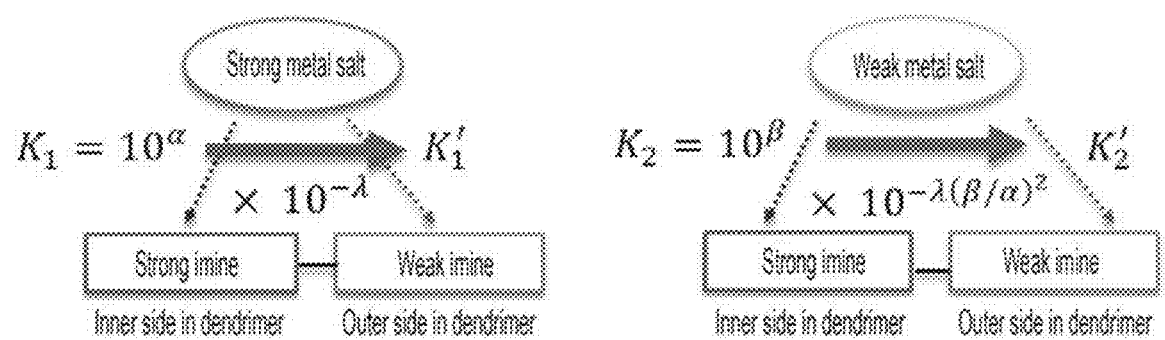
FIG. 28 is a pictorial representation of [Expression 3].

Using the simple theoretical model based on the quantum chemistry, a dimensionless complexation constant is as below.
[Expression 3]—shown in FIG. 28.

The density ratio R of the mixed complex is expressed by the following expression:

$$R = \frac{K_1 \times K_2'}{K_2 \times K_1'} = 10^{\lambda\{1-(\beta/\alpha)^2\}} \qquad \text{[Expression 4]}$$

The relation with the following dimensional complexation constant, which is obtained from experiments, $$\overline{K}_1 = 10^{\overline{\alpha}} M^{-1}$$

$$\overline{K}_2 = 10^{\overline{\beta}} M^{-1} \qquad \text{[Expression 5]}$$

is as shown below assuming the initial density of the imine and the metal salt is $C_0$:

$$K_1 = \frac{C_0}{2} \times \overline{K}_1, \qquad \text{[Expression 6]}$$

$$K_2 = \frac{C_0}{2} \times \overline{K}_2$$

$$\alpha \sim \overline{\alpha} - 5, \beta \sim \overline{\beta} - 5$$

Figure 29:
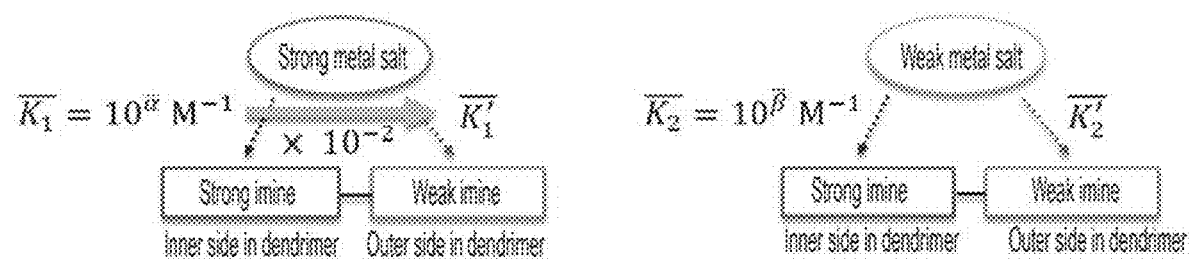
FIG. 29 is a pictorial representation of [Expression 7].

In the phenylazomethine dendrimer with the fourth generation (G4), λ to 2 (K. Yamamoto et al., Bull. Chem. Soc. Jpn., 78, 349 (2005)) and the following relation is satisfied;
[Expression 7]—shown in FIG. 29.

In the phenylazomethine dendrimer with the fourth generation (G4), the following expression $$\overline{K}_1 \approx 10^7 \sim 10^8 M^{-1} \qquad \text{[Expression 8]}$$

is satisfied (K. Yamamoto et al., Bull. Chem. Soc. Jpn., 78, 349 (2005)) and thus, the selectivity in the stepwise assembling is as follows in the relation between the order difference of the complexation constant and the density ratio of the mixed complex.

TABLE 1

| $\overline{\alpha} - \overline{\beta}$ Order difference of complexation constant | Density ratio of mixed complex | Selectivity of stepwise assembling |
|---|---|---|
| 0.0 | 1.0 | 50.0% |
| 0.5 | 4.08 to 7.50 | 80.3 to 88.2% |

TABLE 1-continued

| $\overline{\alpha} - \overline{\beta}$ Order difference of complexation constant | Density ratio of mixed complex | Selectivity of stepwise assembling |
|---|---|---|
| 1.0 | 12.9 to 31.6 | 92.8 to 96.9% |
| 1.5 | 31.6 to 75.0 | 96.9 to 98.7% |
| 2.0 | 59.9 to 100 | 98.4 to 99.0% |

That is to say, regarding two types of mixed complexes, the condition necessary for the selectivity in the stepwise assembling is estimated from the theoretical calculation. However, if it is assumed that a number of, specifically four or more types, particularly five or more types of multiple-metal complexes are precisely assembled stepwise, unpredictable factors that cannot be covered from the theoretical aspects may occur complicatedly, such as the increase in complexation constants to the complex forming parts with the different complexation strength in the dendrimer, counter anion substitution possibility, and the resulting change in complexation strength, all of which need to be considered for each multiple-metal salt. Thus, it is difficult to exactly predict whether the stepwise precise assembling can be achieved or the assembling becomes non-stepwise and random. The present invention has been completed on the basis of the knowledge that the dendrimer complex in which a number of types of multiple-metal complexes are precisely assembled stepwise from the inner layer to the outer layer is obtained in accordance with the experiment results in examples that are described below.

The multiple-metal salt assembly of the dendrimer according to the present invention is formed by the assembling of four or more types of multiple-metal salt compounds with multiple metal species for each of the parts with the different environments in the dendrimer. By reducing the multiple-metal salt assembly of the dendrimer, subnano-metal particles including the alloy of the four or more types of multiple-metals can be produced.

The term "subnano" means that the particle diameter of the particle is in the range of 0.5 to 2.5 nm, particularly in the range of 0.8 to 1.8 nm. A polyhedron atom group, which is formed by a group of some atoms that are partially or entirely bonded to each other directly, is usually called cluster, and in this sense, the subnano metal particles form a cluster.

The multiple-metal salt assembly of the dendrimer can be reduced in, for example, a solution using a reducing agent that has a reducing action for the metal salt compound and that can reduce this to a zero-valent state. Examples of such a reducing agent include sodium borohydride, cyano sodium borohydride, hydrogen, hydrazines, aluminum lithium hydride, diisobutyl aluminum hydride, lithium borohydride, tetra-n-butyl ammonium borohydride, methyl ammonium borohydride, triethyl boron lithium hydride, borane complexes, triacetoxy boron sodium, zinc borohydride, tributyl boron lithium hydride, tributyl boron potassium hydride, Schwartz reagent, Stryker reagent, tributyl tin hydride, sodium hydride, lithium hydride, calcium hydride, benzophenone ketyl radicals, metal naphthalenides, and hydrogen peroxide.

By reducing the multiple-metal salt assembly of the dendrimer in this manner, the subnano metal particles with the size corresponding to the number of assembled metal salt compounds can be covered with the dendrimer and prepared as such. The subnano metal particle obtained by using the multiple-metal salt assembly of the dendrimer according to the present invention may be, for example, the subnano metal particle of 4 elements 13 atoms, 5 elements 13 atoms, 6 elements 17 atoms, and 8 elements 37 atoms. These subnano metal particles may be carried in various types of carrier substances. The carrier substance may be a porous substance, for example, a porous carbon material such as Ketjen black, mesoporous silica, or zeolite. As the subnano metal particles are carried by the carrier substance, the aggregation of the subnano metal particles can be suppressed and in the case of using as the catalyst, the decrease in activity can be suppressed effectively. The subnano metal particles resulting from the dendrimer complex according to the present invention is expected in the use as not just the catalyst and light-emitting materials but also the material for various fields including medicines, electronic functional materials, and environmental suitable materials.

In a conventional method of the oxidation reaction of a hydrocarbon compound free of a polar functional group, metal peroxide is used in a harmful organic solvent for the stoichiometric quantity. In recent years, the clean oxidation reaction with oxygen in the air without the solvent has been researched. Above all, the catalyst carrying nano particles of noble metal in a porous carbon material or metal oxide has been widely researched and such catalyst has been expected as the potential catalyst. The important element in determining the reactivity of such inhomogeneous catalyst is the shape, size, and metal composition of the carried metal nanoparticle. In particular, it has been known that in the area where the size is 2 nm or less, decreasing the particle diameter of the catalyst not just increases the specific surface area but also changes the electron state of the metal surface largely and also changes the reactivity largely; thus, this catalyst has attracted attention in the development of the novel highly functional catalyst. The present inventors synthesized the alloy nanoparticles with a combination of various metals in accordance with a method using the dendrimer that the inventors have developed uniquely, and evaluated the catalyst activity in the oxidation reaction of hydrocarbon under normal pressure using the oxygen molecules in the air as the oxidant. In this researching process, it has been discovered that the alloy nanoparticles including copper atoms and other noble metals are 24 times as active as commercial catalyst that is used in the oxidation reaction of an organic compound. It has been understood that if organic hydroperoxide for the catalyst amount is added using this catalyst, oxidation reaction to ketone or aldehyde of hydrocarbon under normal temperature and normal pressure can be advanced. In addition, by examining the change of the activity by the alloy catalyst with the different metal composition, the composition ratio of the generated product and ketone and organic hydoperoxide that is the intermediate body, and the like, the process of accelerating the reaction by the alloying of the catalyst was clarified.

Light-emitting materials are the field that has been researched in the fundamental and application aspects. So far, various light-emitting molecules have been developed; from now on, the functionalization is required. By using the polymer called dendrimer, which the team of the present inventors has developed uniquely, having a tree structure that is regularly branched repeatedly, the molecule having the light-emitting body precisely arranged can be successfully made, and as the chemical species to be arranged in the molecule, bismuth chloride is focused. By assembling precisely the bismuth chloride in the dendrimer and exhibiting the light-emitting characteristic, the light-emitting dendrimer that can be controlled is achieved.

EXAMPLES

The present invention is described in more detail with reference to Examples; however, the present invention is not limited to these examples.

Example 1

As shown in FIG. 1, the stepwise assembling of the metal salt corresponding to 5 elements 13 atoms to phenylazomethine dendrimer was attempted. The phenylazomethine dendrimer with fourth generation, PyTPM-G4, in which pyridyl triphenyl methane is the core, has the gradual electron density gradient that is gradually lower from the inner layer to the outer layer from the first generation G1 directly bonded to the core to the fourth generation G4 starting from the nitrogen atom at the core. That is to say, there is the stepwise complex forming part because of the difference in imine basicity; from the core, 1 equivalent to the pyridine part, 1 equivalent and 3 equivalents to the imine part in the first generation, and 2 equivalents and 6 equivalents to the imine part in the second generation. In the present example, stepwise assembling of five types of multiple-metal salts, which have been conventionally unknown, to the PyTPM-G4 was attempted.

Figure 2:
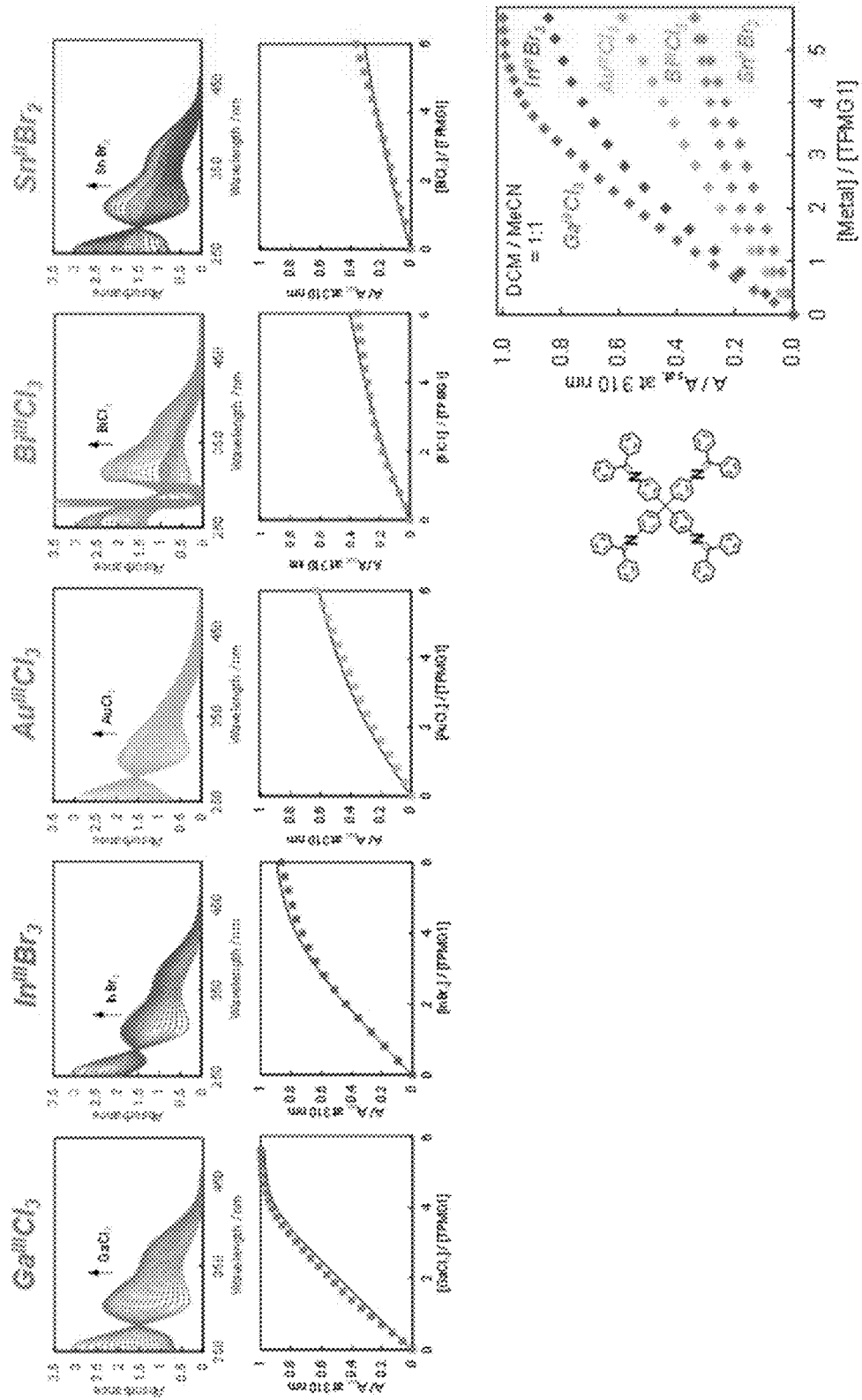
FIG. 2 is graphs showing the change of the ultraviolet-visible absorption spectrum when $GaCl_3$, $InBr_3$, $AuCl_3$, $BiCl_3$, and $SnBr_2$ are dripped in a solution of TPM-G1, and showing results of plotting A/Asat. at 310 nm to the density ratio: metal salt/TPM-G1.

First, as illustrated in FIG. 2, the change of the ultraviolet-visible absorption spectrum when $GaCl_3$, $InBr_3$, $AuCl_3$, $BiCl_3$, and $SnBr_2$ were dripped into the solution of phenylazomethine dendrimer with the first generation, TPM-G1, in which tetraphenylmethane is the core, was measured and the absorbance A/Asat. at 310 nm was plotted to the density ratio: metal salt/TPM-G1.

An acetonitrile (AN) solution of the metal salt was dripped to a DCM/AN=1:1 solution (TPM-G1, 30 μM) in which the dendrimer was dissolved in a mixed solvent of dichloromethane (DCM) and acetonitrile (AN). The measurement was performed at 20° C.

As shown in FIG. 2, the complexation strength of five metal salts varies, and the complexation strength is in the order of $GaCl_3$, $InBr_3$, $AuCl_3$, $BiCl_3$, and $SnBr_2$. These results indicate that each metal salt has the different complexation constant (G1) under the same solvent condition.

Figure 3:
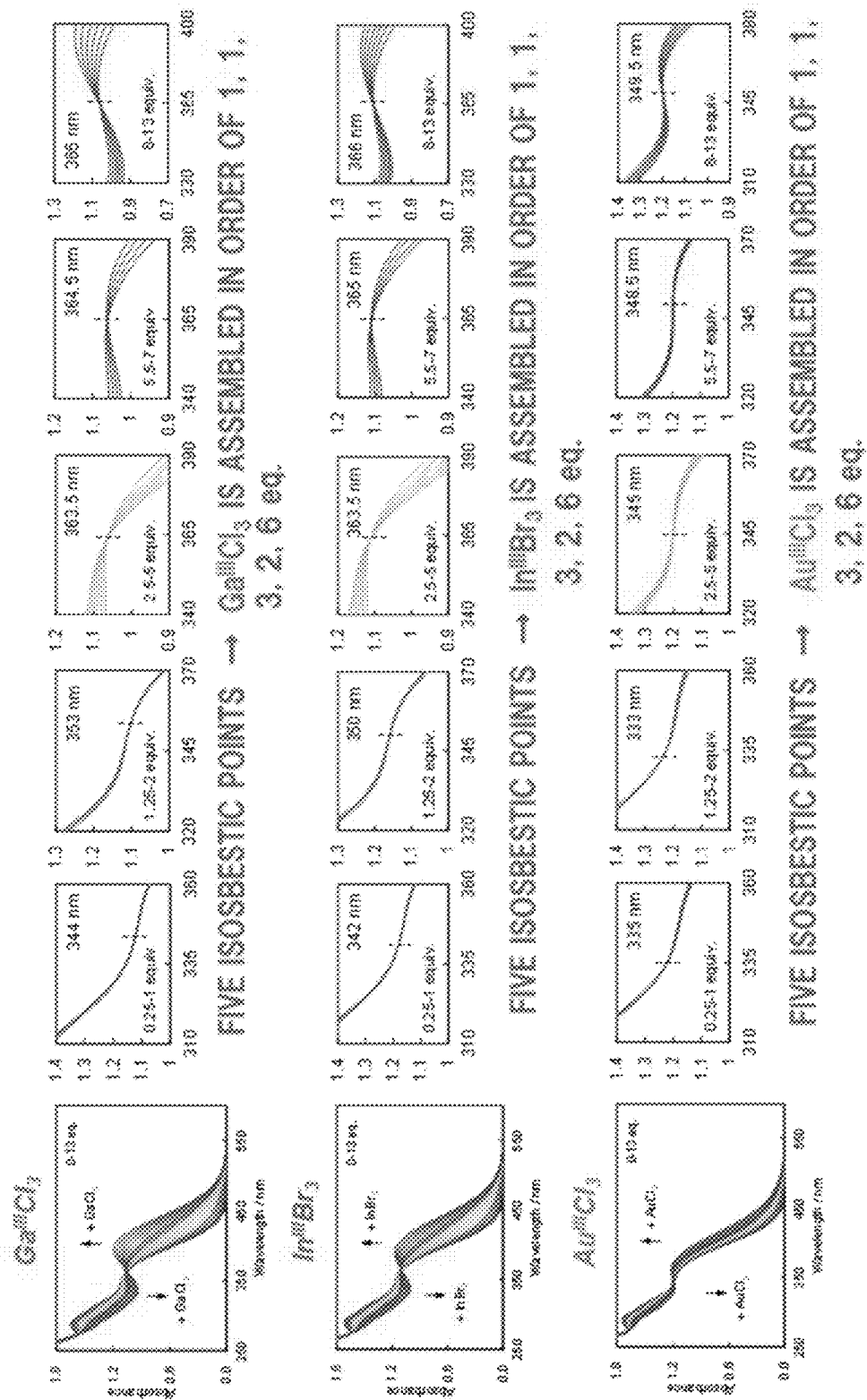
FIG. 3 shows the change of the ultraviolet-visible absorption spectrum when $GaCl_3$, $InBr_3$, $AuCl_3$, $BiCl_3$, and $SnBr_2$ are dripped each by up to 13 equivalents in a solution of PyTPM-G4.
Figure 4:
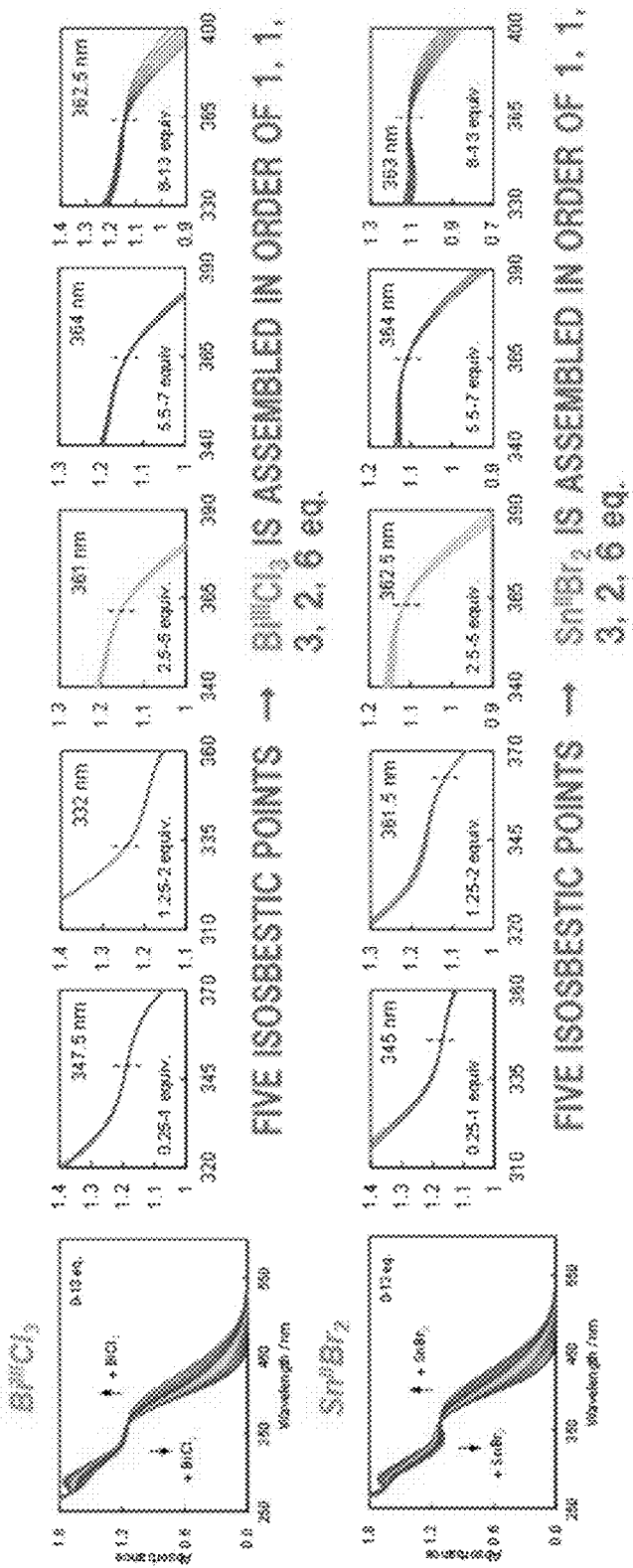
FIG. 4 shows the change of the ultraviolet-visible absorption spectrum when $BiCl_3$ and $SnBr_2$ are dripped each by 13 equivalents in the solution of PyTPM-G4.

Next, to the PyTPM-G4 solution, $GaCl_3$, $InBr_3$, $AuCl_3$, $BiCl_3$, and $SnBr_2$ were dripped each by up to 13 equivalents so as to attempt the assembling. FIG. 3 shows the change of the ultraviolet-visible absorption spectrum when $GaCl_3$, $InBr_3$, $AuCl_3$, $BiCl_3$, and $SnBr_2$ were dripped each by up to 13 equivalents to the solution of PyTPM-G4. FIG. 4 shows the change of the ultraviolet-visible absorption spectrum when $BiCl_3$ and $SnBr_2$ were dripped each by 13 equivalents to the solution of PyTPM-G4. To a DCM/AN=1:1 solution (PyTPM-G4, 3 μM) in which dendrimer was dissolved in a mixed solvent of dichloromethane (DCM) and acetonitrile (AN), an acetonitrile (AN) solution of metal salt was dripped. The measurement was performed at 20° C.

In any of $GaCl_3$, $InBr_3$, $AuCl_3$, $BiCl_3$, and $SnBr_2$, five isosbestic points were observed and it has been confirmed that these were assembled in the order of 1, 1, 3, 2, and 6 equivalents. From FIG. 2 to FIG. 4, it has been made clear that the five types of metal salts were successfully assembled to PyTPM-G4 and the conditions of the stepwise assembling are: the metal salts can be precisely assembled to PyTPM-G4 under the same solvent condition, the metal salts have different complexation constants (G1) under the same solvent condition, and the metal salts can be precisely assembled to PyTPM-G4 by 13 equivalents under the same solvent condition.

Figure 5:
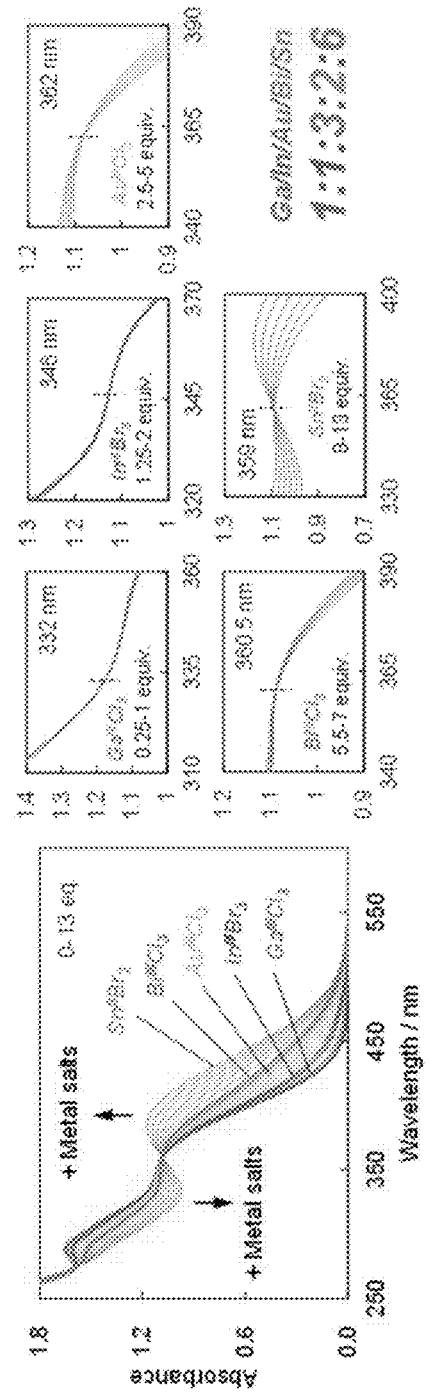
FIG. 5 shows the change of the ultraviolet-visible absorption spectrum when $GaCl_3$, $InBr_3$, $AuCl_3$, $BiCl_3$, and $SnBr_2$ are dripped in the solution of PyTPM-G4 in this order by 1, 1, 3, 2, and 6 equivalents up to 13 equivalents.
Figure 5:
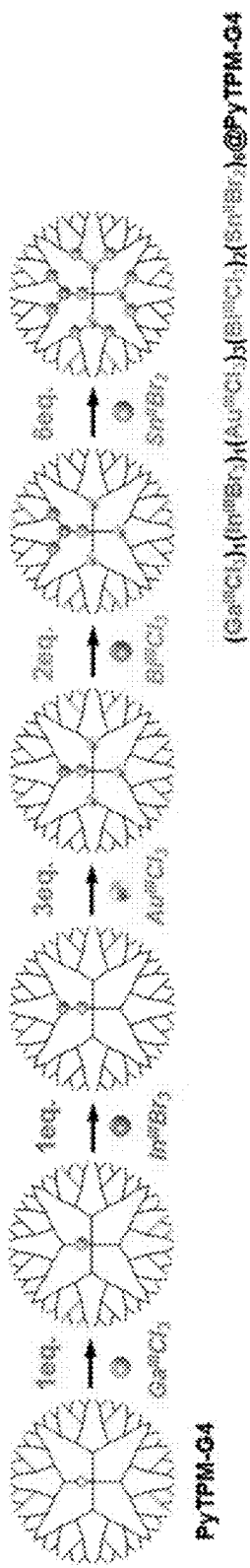

Next, $GaCl_3$, $InBr_3$, $AuCl_3$, $BiCl_3$, and $SnBr_2$ were dripped to the solution of PyTPM-G4 in this order by 1, 1, 3, 2, and 6 equivalents up to 13 equivalents and the assembling was attempted. FIG. 5 shows the change of the ultraviolet-visible absorption spectrum at that time. To a DCM/AN=1:1 solution (PyTPM-G4, 3 μM) in which dendrimer was dissolved in a mixed solvent of dichloromethane (DCM) and acetonitrile (AN), an acetonitrile (AN) solution of metal salt was dripped. The measurement was performed at 20° C. Five isosbestic points were observed, and it has been confirmed that these were assembled in the order of 1, 1, 3, 2, and 6 equivalents. This has clarified that five types of metal salts were successfully assembled to PyTPM-G4 without the change of the assembling order.

Figure 6:
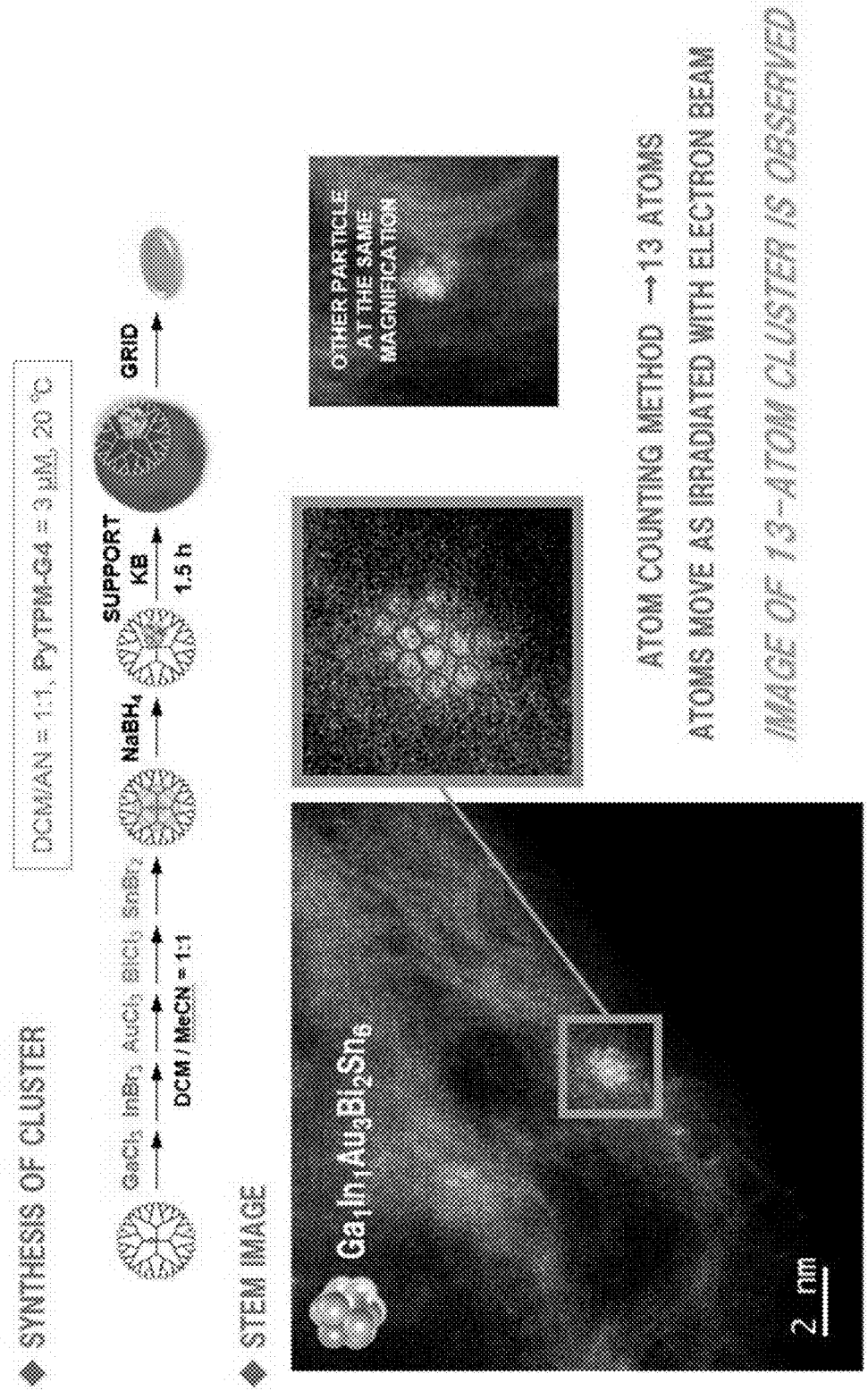
FIG. 6 shows the procedure of synthesizing a subnano alloy cluster from a dendrimer complex having five types of metal salts assembled precisely to PyTPM-G4, and HAADF-STEM images of the 13-atom cluster.
Figure 7:
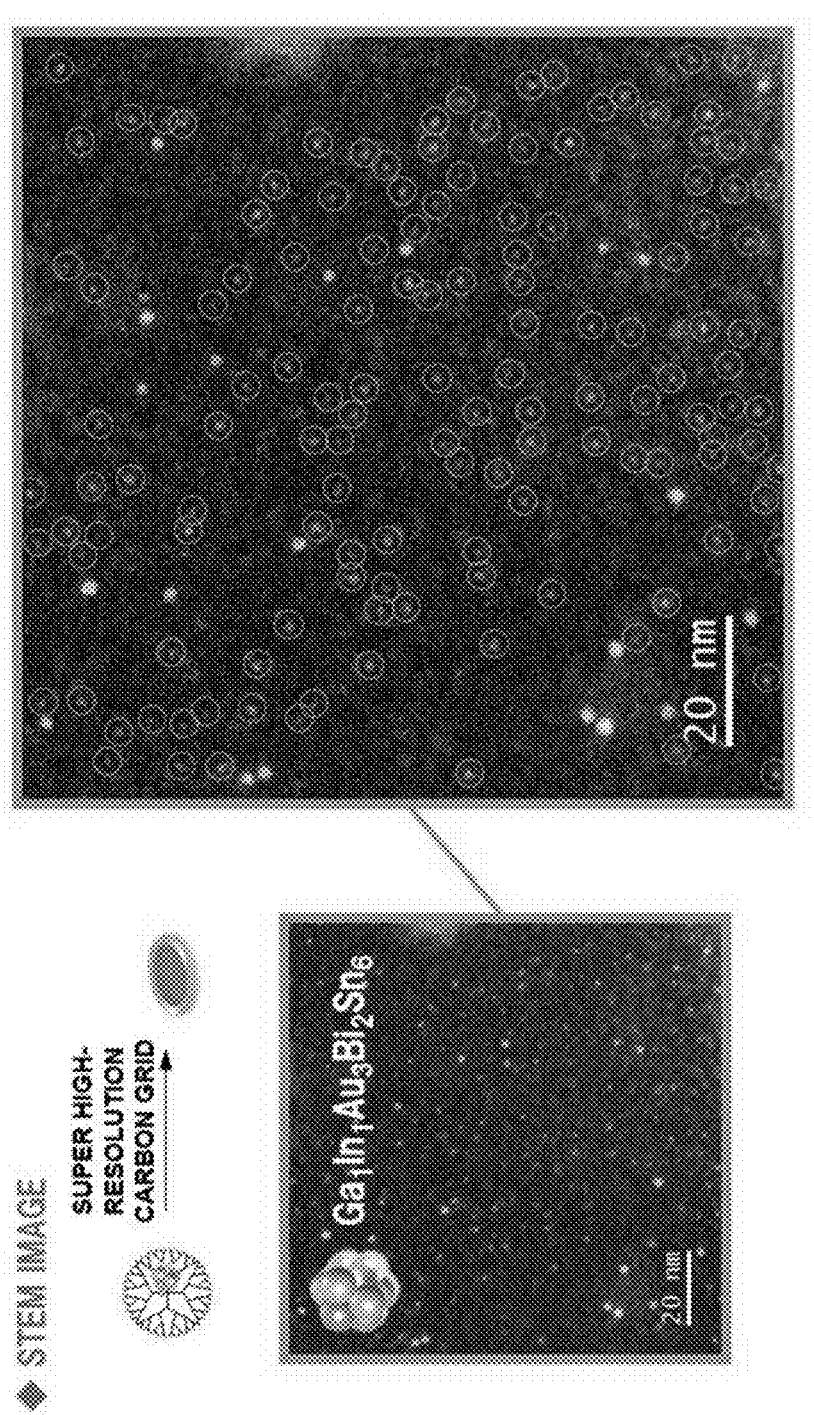
FIG. 7 shows HAADF-STEM images of the 13-atom cluster synthesized from the dendrimer complex having five types of metal salts assembled precisely to PyTPM-G4.
Figure 8:
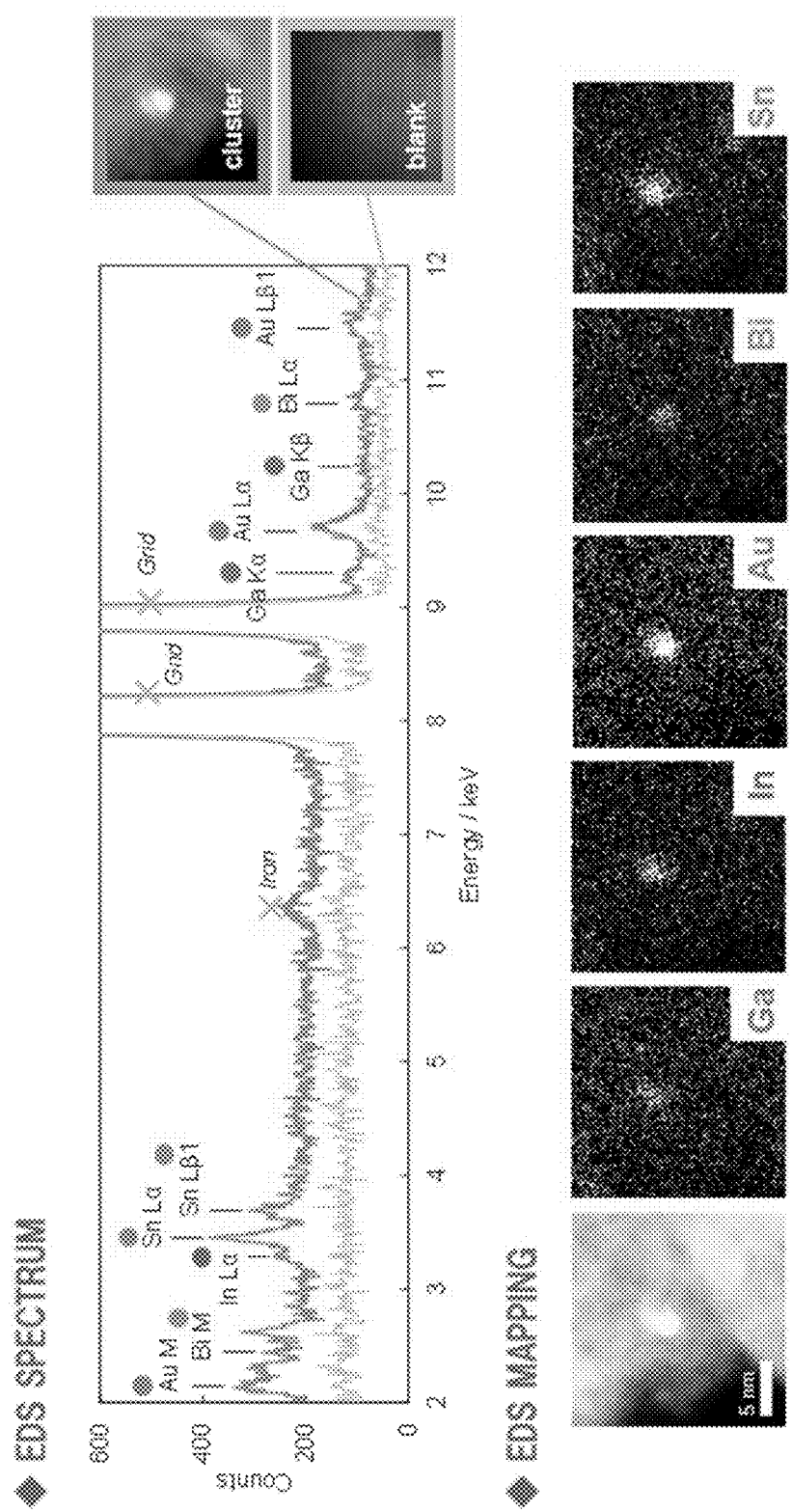
FIG. 8 shows EDS spectra and EDS mapping of the 13-atom cluster synthesized from the dendrimer complex having five types of metal salts assembled precisely to PyTPM-G4.

Next, the synthesis of subnano alloy cluster from the dendrimer complex having five types of metal salts assembled precisely to the PyTPM-G4 was attempted. FIG. 6 shows the synthesis procedure. The PyTPM-G4 complex of five types of metal salts obtained above was mixed with a $NaBH_4$ solution and the mixture was reduced. Thus, 5 element 13 atoms phenylazomethine dendrimer subnano metal particles@PyTPMG4 dendrimer was obtained. Ketjen black as the carrier agent was added and the dendrimer was carried (1.5 hr). FIG. 6 is observation photographs by HAADF-STEM (High-angle Annular Dark Field Scanning TEM) about this carrying body, and white bright spots indicate subnano particles. By an atom counting method, an image of 13-atom clusters was observed. FIG. 7 shows that a number of particles with a size of about 1 nm were observed and the subnano cluster was synthesized with high yield. FIG. 8 shows EDS spectra and EDS mapping of the 13-atom cluster synthesized from the dendrimer complex in which five types of metal salts were precisely assembled to PyTPM-G4. Peaks of Ga, In, Au, Bi, and Sn were observed in the cluster, and the generation of the five-element cluster was confirmed.

Example 2

Figure 9:
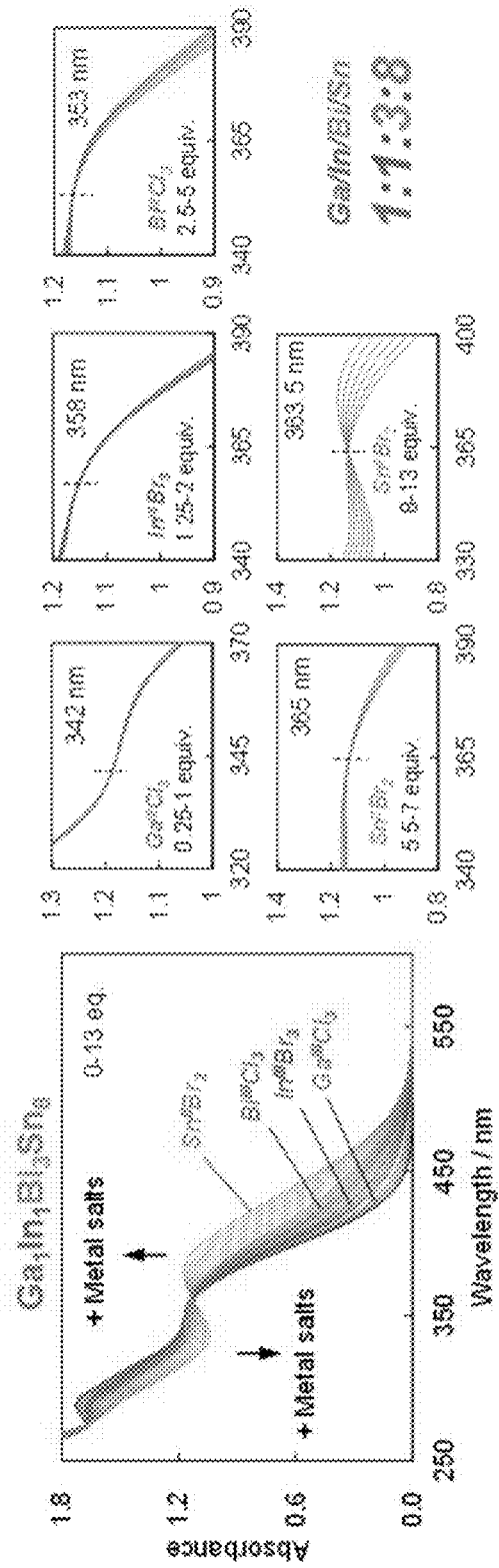
FIG. 9 shows the change of the ultraviolet-visible absorption spectrum when $GaCl_3$, $InBr_3$, $BiCl_3$, and $SnBr_2$ are dripped in the solution of PyTPM-G4 in this order by 1, 1, 3, and 8 equivalents up to 13 equivalents.
Figure 9:
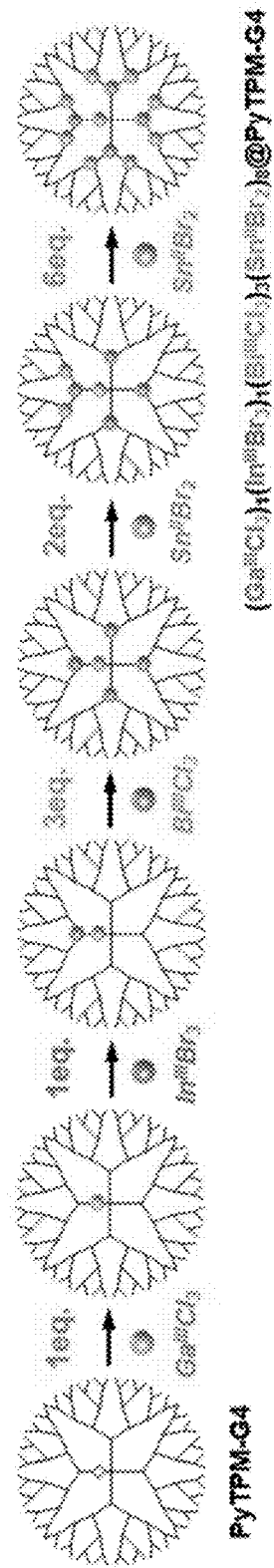
Figure 10:
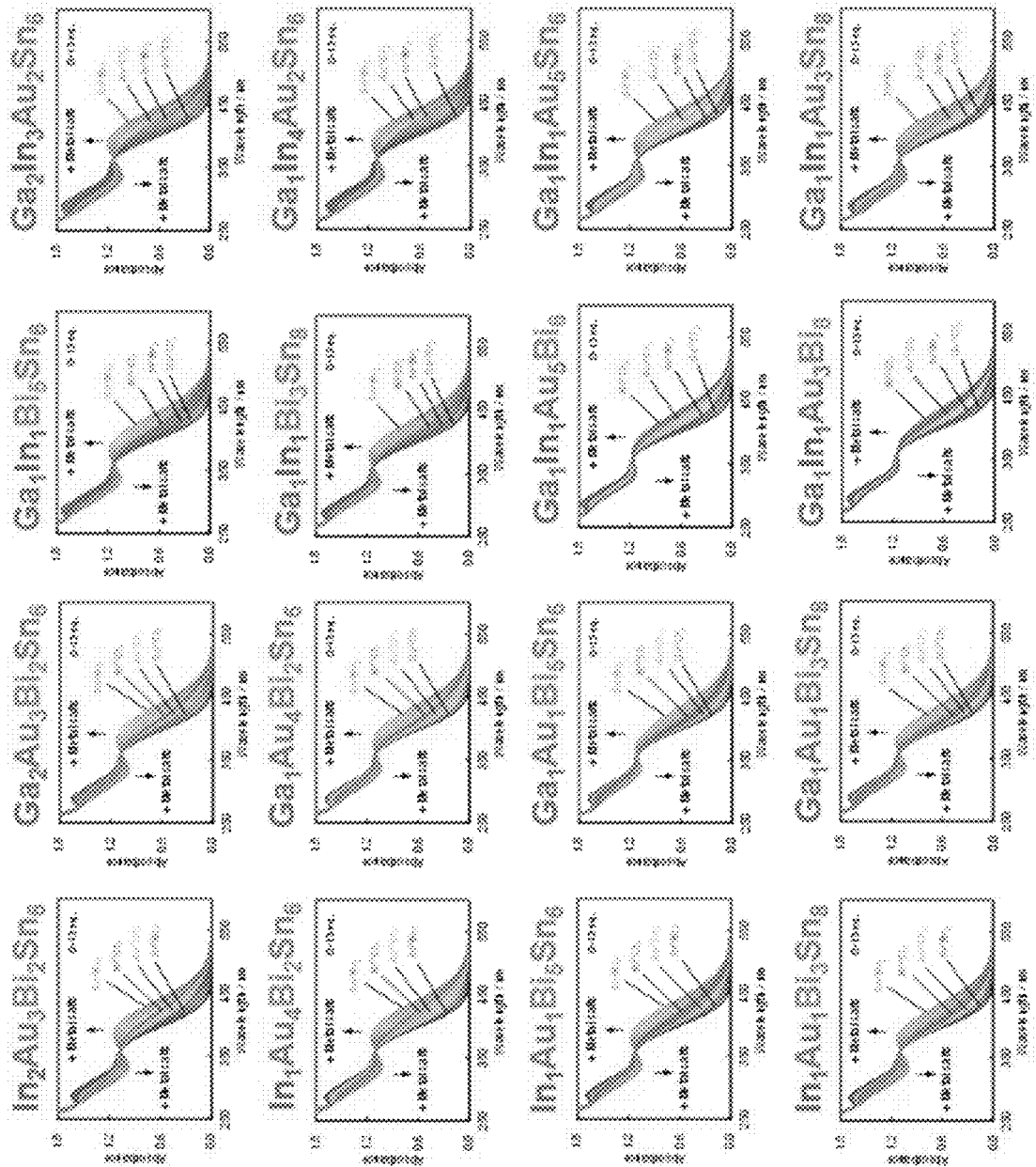
FIG. 10 shows the change of the ultraviolet-visible absorption spectrum when the metal salts with various compositions and composition ratios are dripped in order in the solution of PyTPM-G4 by up to 13 equivalents.

FIG. 9 and FIG. 10 show that the stepwise assembling of the metal salt corresponding to 4 elements 13 atoms to the phenylazomethine dendrimer was attempted FIG. 9 shows the change of the ultraviolet-visible absorption spectrum when $GaCl_3$, $InBr_3$, $BiCl_3$, and $SnBr_2$ were dripped in the solution of PyTPM-G4 in order by 1, 1, 3, and 8 equivalents up to 13 equivalents. To a DCM/AN=1:1 solution (PyTPM-G4, 3 μM) in which dendrimer was dissolved in a mixed solvent of dichloromethane (DCM) and acetonitrile (AN), an acetonitrile (AN) solution of metal salt was dripped. The measurement was performed at 20° C. Five isosbestic points were observed, and it has been confirmed that these were assembled in the order of 1, 1, 3, and 8 equivalents. This has clarified that four types of metal salts were successfully assembled to PyTPM-G4 $((GaCl_3)_1 (InBr_3)_1(BiCl_3)_3(SnBr_2)_8$@PyTPM-G4) without the change of the assembling order.

FIG. 10 shows the change of the ultraviolet-visible absorption spectrum when the metal salts with various compositions and composition ratios were dripped in order in the solution of PyTPM-G4 by up to 13 equivalents. Regarding the metal compositions $In_2Au_3Bi_2Sn_6$, $In_1Au_4Bi_2Sn_6$, $In_1Au_1Bi_5Sn_6$, $In_1Au_1Bi_3Sn_8$, $Ga_2Au_3Bi_2Sn_6$, $Ga_1Au_4Bi_2Sn_6$, $Ga_1Au_1Bi_5Sn_6$, $Ga_1Au_1Bi_3Sn_8$, $Ga_1In_1Bi_5Sn_6$, $Ga_1In_1Bi_3Sn_8$, $Ga_1In_1Au_5Bi_6$, $Ga_1In_1Au_3Bi_8$, $Ga_2In_3Au_2Sn_6$, $Ga_1In_4Au_2Sn_6$, $Ga_1In_1Au_5Sn_6$, and $Ga_1In_1Au_3Sn_8$, five isosbestic points were observed when the metal salts were added sequentially, and it has been confirmed that by reducing one type of element with 13 atoms from the stepwise assembling of the metal salts corresponding to 5 elements 13 atoms in Example 1 to the phenylazomethine dendrimer, the dendrimer complex in which the multiple-metal salt is stepwise assembled in various compositions can be obtained.

Example 3

Figure 11:
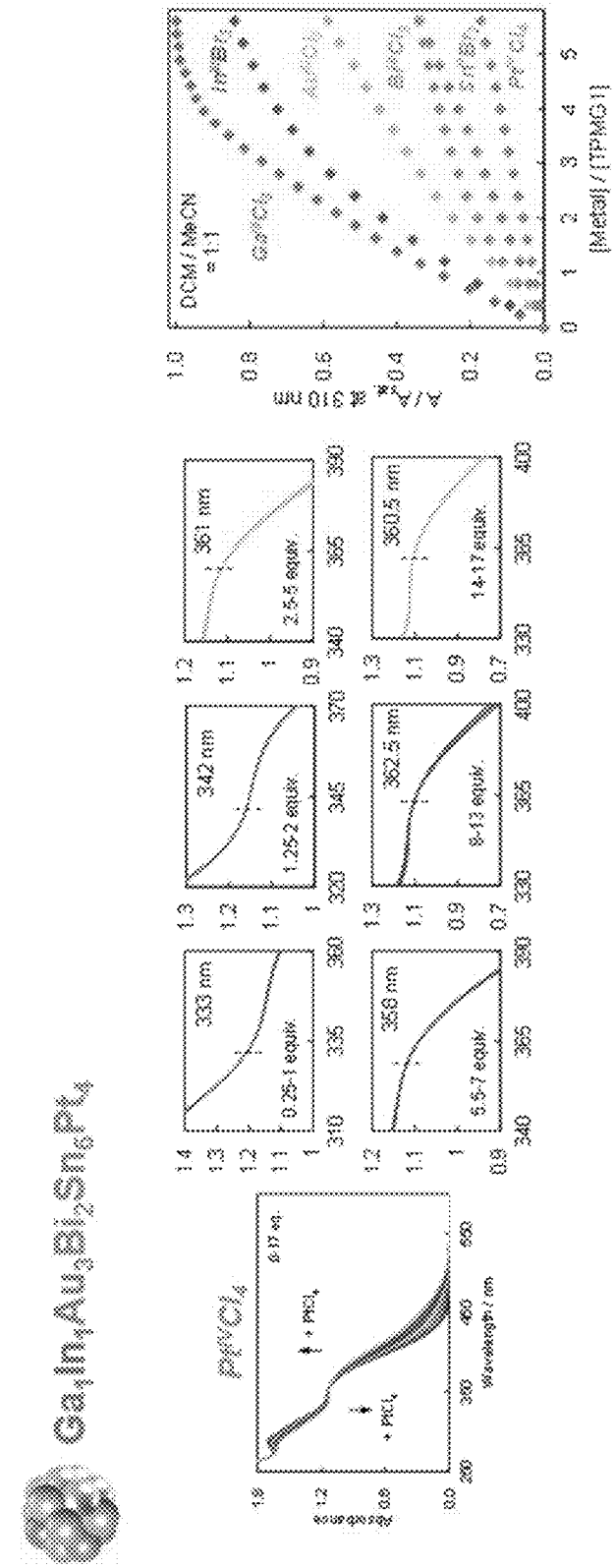
FIG. 11 is graphs showing the change of the ultraviolet-visible absorption spectrum when $PtCl_4$ is dripped in the solution of PyTPM-G4 by up to 17 equivalents, and showing the results of plotting A/Asat. at 310 nm to the density ratio: metal salt/TPMG1 when $GaCl_3$, $InBr_3$, $AuCl_3$, $BiCl_3$, $SnBr_2$, and $PtCl_4$ are dripped in the solution of TPM-G1.
Figure 11:
Figure 12:
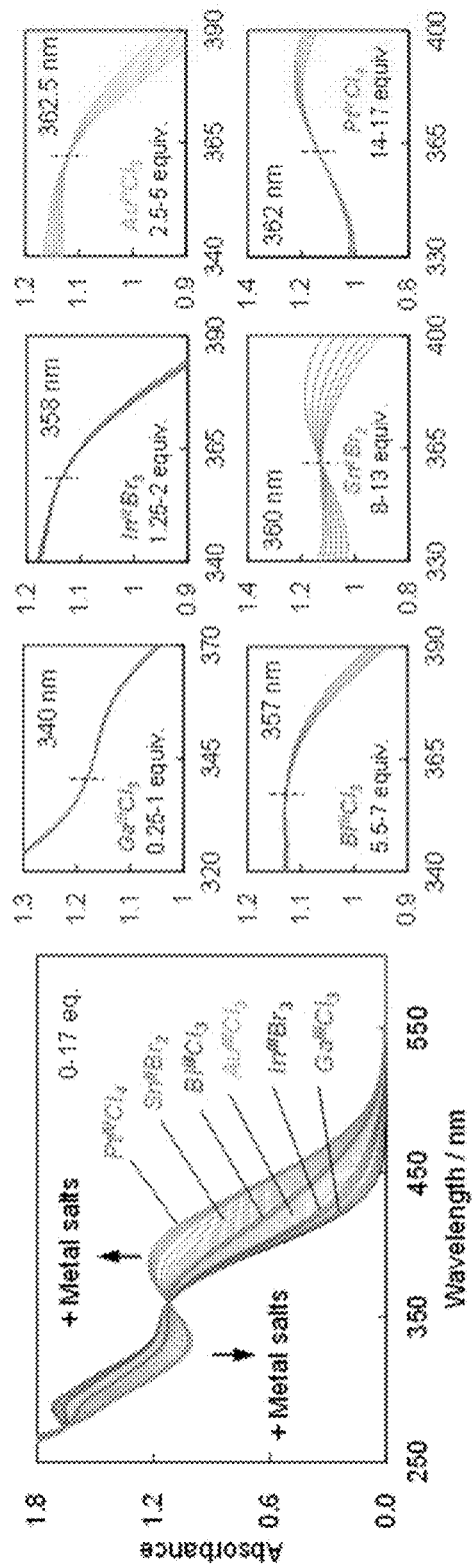
FIG. 12 shows the change of the ultraviolet-visible absorption spectrum when $GaCl_3$, $InBr_3$, $AuCl_3$, $BiCl_3$, $SnBr_2$, and $PtCl_4$ are dripped in the solution of PyTPM-G4 in this order by 1, 1, 3, 2, 6, and 4 equivalents up to 17 equivalents.
Figure 12:
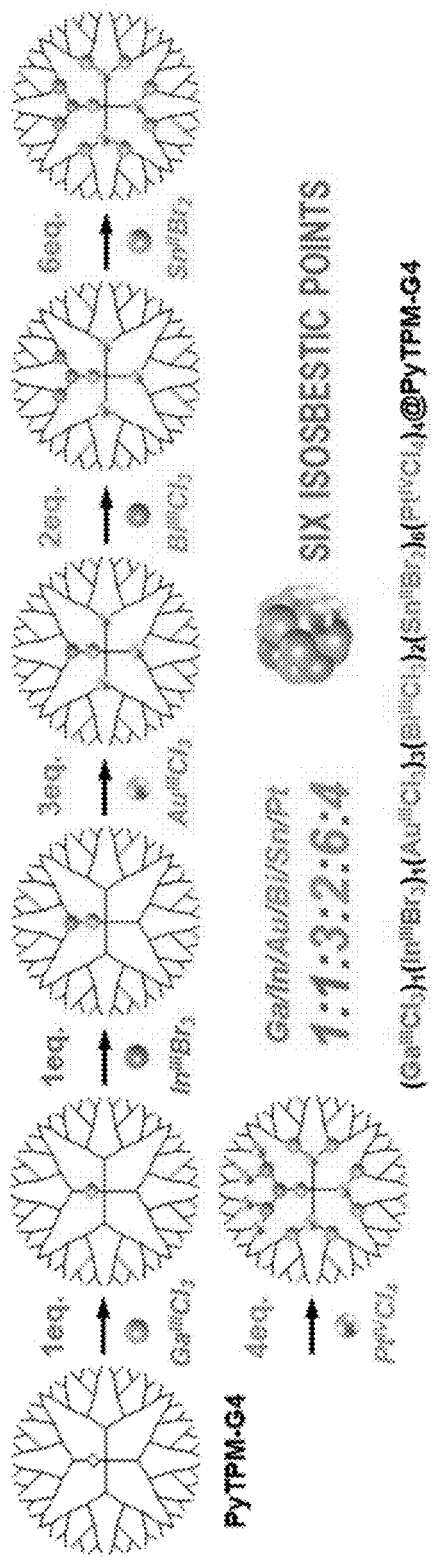

Next, on the basis of the results from Example 1, the stepwise assembling of the metal salt corresponding to 6 elements 17 atoms to the phenylazomethine dendrimer was attempted. FIG. 11 shows, in the left part, the change of the ultraviolet-visible absorption spectrum when $PtCl_4$ was dripped in the solution of PyTPM-G4 by up to 17 equivalents. Six isosbestic points were observed and it has been confirmed that these were assembled in the order of 1, 1, 3, 2, 6, and 4 equivalents. FIG. 11 shows, in the right part, the change of the ultraviolet-visible absorption spectrum when $GaCl_3$, $InBr_3$, $AuCl_3$, $BiCl_3$, $SnBr_2$, and $PtCl_4$ were dripped in the solution of phenylazomethine dendrimer TPM-G1 with the first generation including tetraphenylmethane as a core was measured and the absorbance A/Asat. at 310 nm was plotted to the density ratio: metal salt/TPM-G1. The complexation strength of six types of metal salts varied and the complexation strength was in the order of $GaCl_3$, $InBr_3$, $AuCl_3$, $BiCl_3$, $SnBr_2$, and $PtCl_4$. The results indicate that the metal salts have different complexation constants (G1) under the same solvent condition.

Next, $GaCl_3$, $InBr_3$, $AuCl_3$, $BiCl_3$, $SnBr_2$, and $PtCl_4$ were dripped in the solution of PyTPM-G4 in order by 1, 1, 3, 2, 6, and 4 equivalents up to 17 equivalents and the assembling was attempted. FIG. 5 shows the change of the ultraviolet-visible absorption spectrum at this time. To a DCM/AN=1:1 solution (PyTPM-G4, 3 µM) in which dendrimer was dissolved in a mixed solvent of dichloromethane (DCM) and acetonitrile (AN), an acetonitrile (AN) solution of metal salt was dripped. The measurement was performed at 20° C. Six isosbestic points were observed, and it has been confirmed that these were assembled in the order of 1, 1, 3, 2, 6, and 4 equivalents. This has clarified that six types of metal salts were successfully assembled precisely to PyTPM-G4 without the change of the assembling order.

Example 4

Next, the stepwise assembling of the metal salt corresponding to 8 elements 37 atoms to the phenylazomethine dendrimer was attempted.

Figure 13:
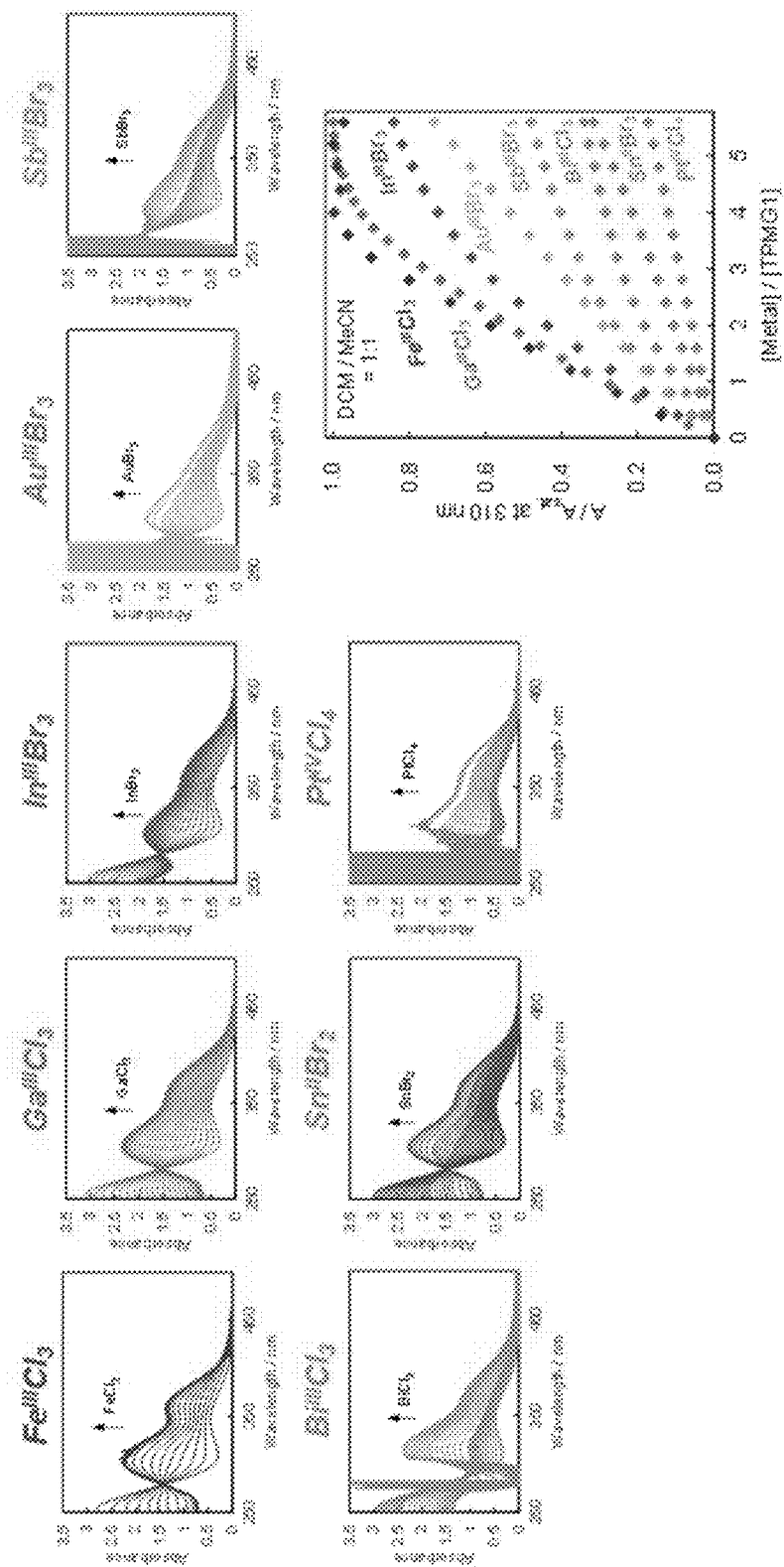
FIG. 13 is graphs showing the change of the ultraviolet-visible absorption spectrum when $FeCl_3$, $GaCl_3$, $InBr_3$, $AuBr_3$, $SbBr_3$, $BiCl_3$, $SnBr_2$, and $PtCl_4$ are dripped in the solution of TPM-G1, and showing results of plotting A/Asat. at 310 nm to the density ratio: metal salt/TPM-G1.

First, as shown in FIG. 13, the change of the ultraviolet-visible absorption spectrum when $FeCl_3$, $GaCl_3$, $InBr_3$, $AuBr_3$, $SbBr_3$, $BiCl_3$, $SnBr_2$, and $PtCl_4$ were dripped in the solution of phenylazomethine dendrimer TPM-G1 with the first generation including tetraphenylmethane as a core was measured and the absorbance A/Asat. at 310 nm was plotted to the density ratio: metal salt/TPM-G1.

To a DCM/AN=1:1 solution (TPM-G1, 30 µM) in which dendrimer was dissolved in a mixed solvent of dichloromethane (DCM) and acetonitrile (AN), an acetonitrile (AN) solution of metal salt was dripped. The measurement was performed at 20° C.

As shown in FIG. 13, the complexation strength of eight types of metal salts varied and the complexation strength was in the order of $FeCl_3$, $GaCl_3$, $InBr_3$, $AuBr_3$, $SbBr_3$, $BiCl_3$, $SnBr_2$, and $PtCl_4$. The results indicate that the metal salts have different complexation constants (G1) under the same solvent condition.

Figure 14:
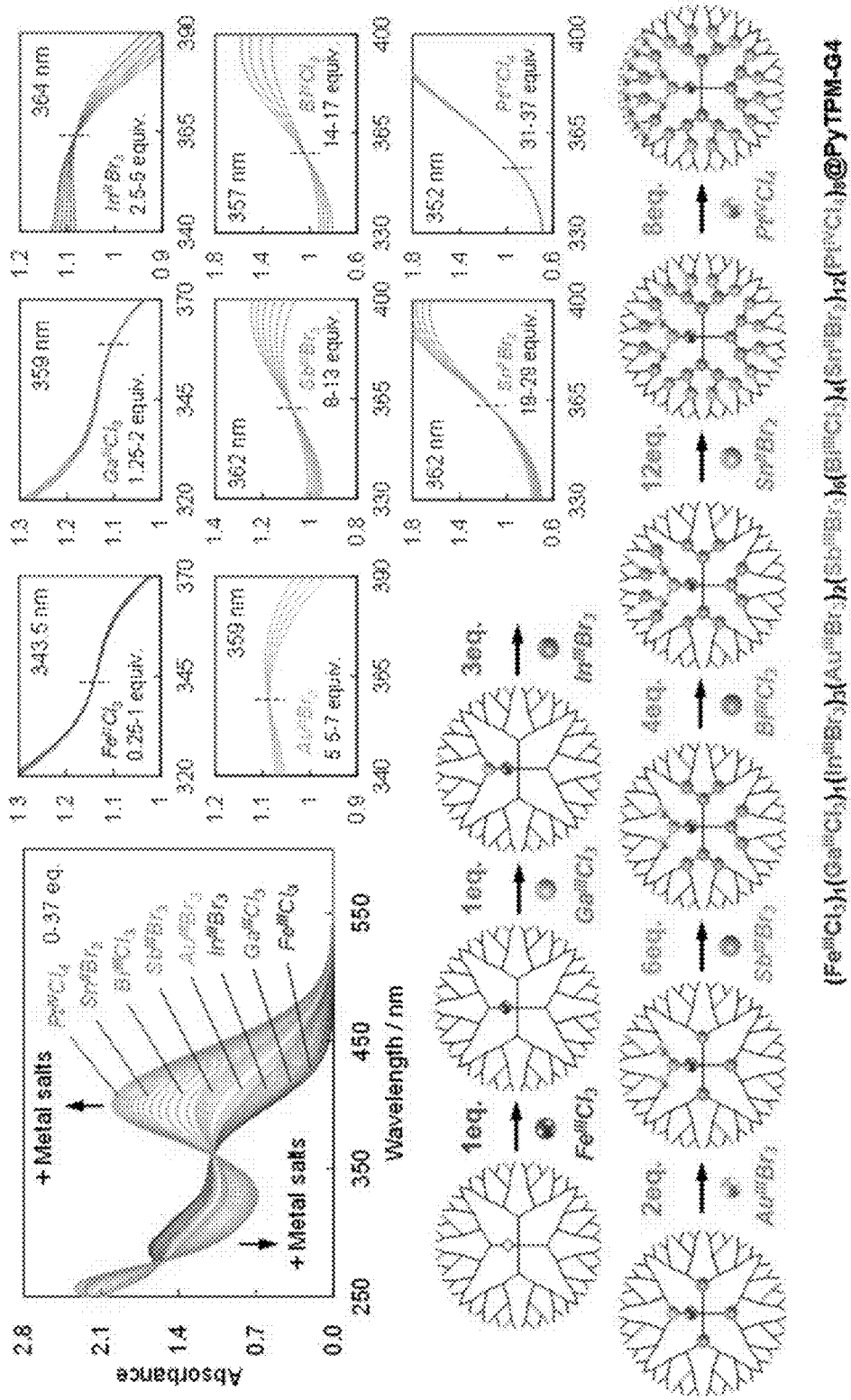
FIG. 14 is graphs showing the change of the ultraviolet-visible absorption spectrum when $FeCl_3$, $GaCl_3$, $InBr_3$, $AuBr_3$, $SbBr_3$, $BiCl_3$, $SnBr_2$, and $PtCl_4$ are dripped in the solution of PyTPM-G4 in this order by 1, 1, 3, 2, 6, 4, 12, and 8 equivalents by up to 37 equivalents.

Next, $FeCl_3$, $GaCl_3$, $InBr_3$, $AuBr_3$, $SbBr_3$, $BiCl_3$, $SnBr_2$, and $PtCl_4$ were dripped in the solution of PyTPM-G4 in order by 1, 1, 3, 2, 6, 4, 12, and 8 equivalents up to 37 equivalents and the assembling was attempted. FIG. 14 shows the change of the ultraviolet-visible absorption spectrum at this time. To a DCM/AN=1:1 solution (PyTPM-G4, 3 µM) in which dendrimer was dissolved in a mixed solvent of dichloromethane (DCM) and acetonitrile (AN), an acetonitrile (AN) solution of metal salt was dripped. The measurement was performed at 20° C. Eight isosbestic points were observed, and it has been confirmed that these were assembled in the order of 1, 1, 3, 2, 6, 4, 12, and 8 equivalents. This has clarified that eight types of metal salts were successfully assembled precisely to PyTPM-G4 without the change of the assembling order.

Reference Example 1

The effect of the counter anion of metal salt to the complexation strength was examined.

Figure 15:
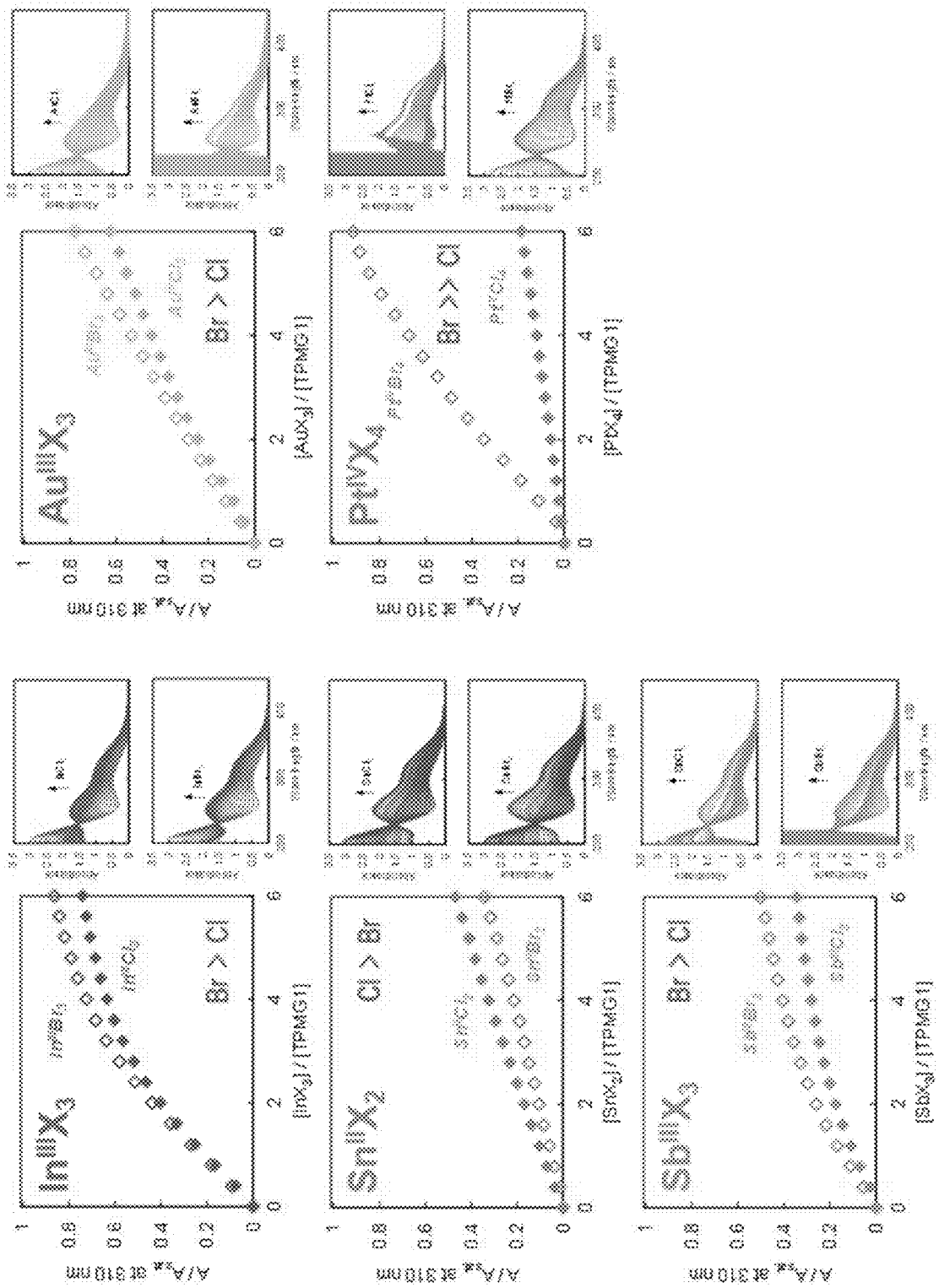
FIG. 15 is graphs showing the change of the ultraviolet-visible absorption spectrum when various types of metal salts are dripped in the solution of TPM-G1, and showing results of plotting the absorbance A/Asat. at 310 nm to the density ratio: metal salt/TPM-G1.

The ultraviolet-visible absorption spectrum when the metal salt shown in FIG. 15 was dripped in the solution of phenylazomethine dendrimer with the first generation, TPM-G1, in which tetraphenylmethane is the core, was measured and the absorbance A/Asat. at 310 nm was plotted to the density ratio: metal salt/TPM-G1.

To a DCM/AN 1:1 solution (TPM-G1, 30 µM) in which dendrimer was dissolved in a mixed solvent of dichloromethane (DCM) and acetonitrile (AN), an acetonitrile (AN) solution of metal salt was dripped. The measurement was performed at 20° C. Regarding the same metal species (In, Sn, Sb, Au, Pt), two types of halogens (Br and Cl) were compared.

As a result, as shown in FIG. 15, the following tendency of the complexation strength was observed: Br>Cl for $In^{III}X_3$, Cl>Br for $Sn^{II}X_2$, Br>Cl for $Sb^{III}X_3$, Br>Cl for $Au^{III}X_3$, and Br>>Cl for $PtX_4$. This is mainly because of the electronic effect of the halogen atom X. Thus, it has been confirmed that the coordination trend can be adjusted by the counter ion.

Next, it was attempted to control the coordination trend by changing the counter anion of the metal salt to the organic ligand.

Figure 16:
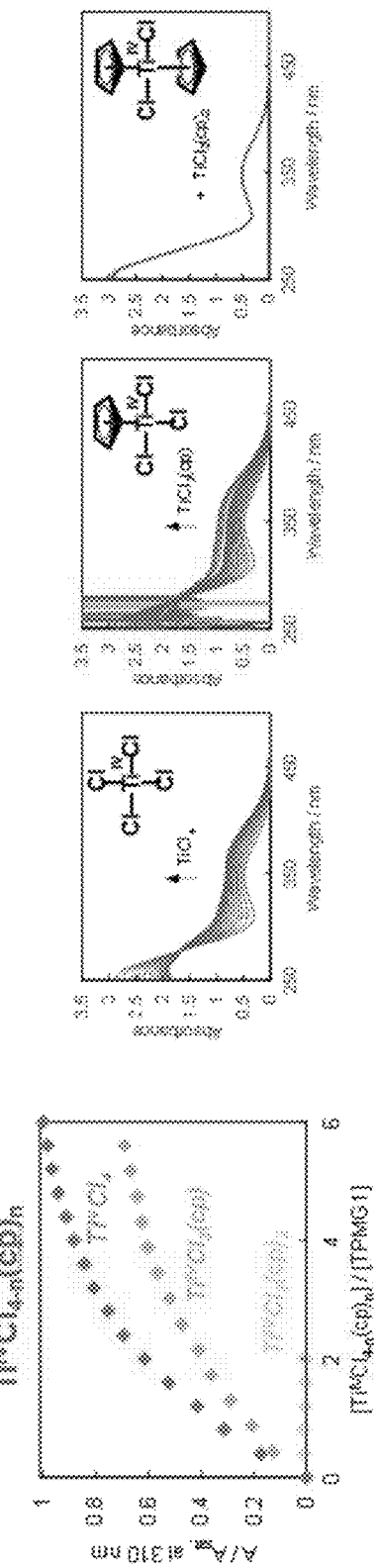
FIG. 16 is graphs obtained by measuring the change of the ultraviolet-visible absorption spectrum when the solution in which titanium tetrachloride and the counter anion thereof are changed to cyclopentadienyl ligand (cp) is dripped in the solution of TPM-G1, and plotting the absorbance A/Asat. at 310 nm to the density ratio: metal salt/TPM-G1.

In FIG. 16, the change of the coordination trend when the counter anion of titanium tetrachloride was changed to cyclopentadienyl ligand (cp) using the model compound TPM-G1 was plotted. The solvent is DCM(dichloromethane)/THF (tetrahydrofuran)=3:1, the density of TPM-G1 is 30 µM, and the temperature is 20° C. In order to examine the effect of the ligand correctly, the oxidation number of the metal is the same in the comparison.

The results indicate that the coordination trend increases in the order of $Ti^{IV}Cl_4>Ti^{IV}Cl_3(cp)>Ti^{IV}Cl_2(cp)_2$. By using the stereoscopic effect of the ligand in addition to the electronic effect of the halogen atom, the coordination trend can be successfully controlled widely.

By using the electronic and stereoscopic effect of the counter anion of the metal salt as described above, it is possible to change the order of assembling the two types of metals.

Figure 17:
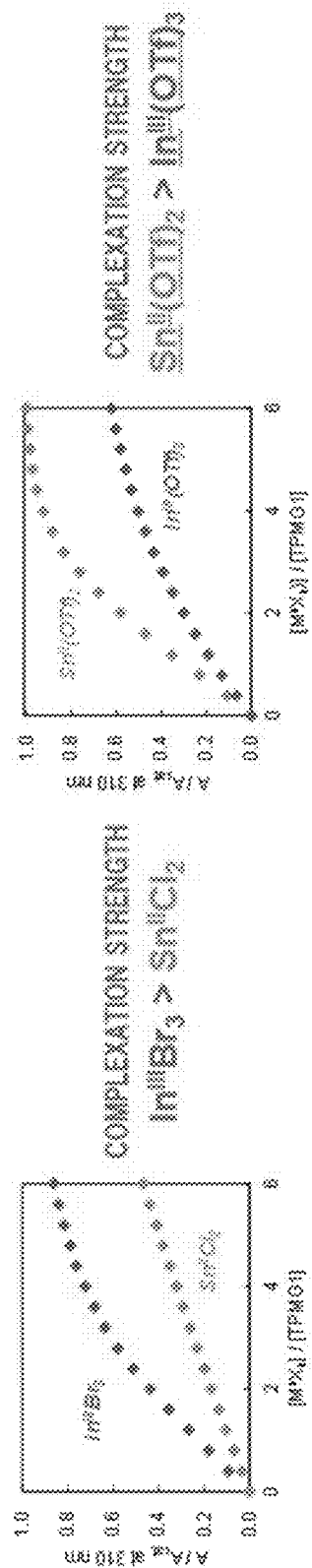
FIG. 17 is graphs obtained by measuring the change of the ultraviolet-visible absorption spectrum when chloride and bromide (Cl, Br) of indium and tin and trifluoromethane sulfonate (OTf) are dripped in the solution of TPM-G1, and plotting the absorbance A/Asat. at 310 nm to the density ratio: metal salt/TPM-G1.

FIG. 17 shows the plots for comparing the coordination trend of chloride and bromide (Cl, Br) of indium and tin and trifluoromethane sulfonate (OTf) using the model compound TPM-G1. In the case of the chloride and bromide (Cl, Br) of indium and tin, the solvent is DCM (dichloromethane)/AN (acetonitrile)=1:1, the density of TPM-G1 is 30 μM, and the temperature is 20° C. In the case of the trifluoromethane sulfonate (OTf), the solvent is THF (tetrahydrofuran), the density of TPM-G1 is 30 μM, and the temperature is 20° C.

As shown in the drawing, the coordination trend of indium (In) and tin (Sn) can be reversed. This suggests that, in the mixing and assembling of two or more types of metals, the order of assembling these can be controlled.

Reference Example 2

Metal assembling using the dummy coordination trend was attempted.
(Assembling by Organic Cation)

By using the coordination trend of, not the metal salt itself, but the organic cation, the assembling of metal as the counter anion was attempted.

Figure 18:
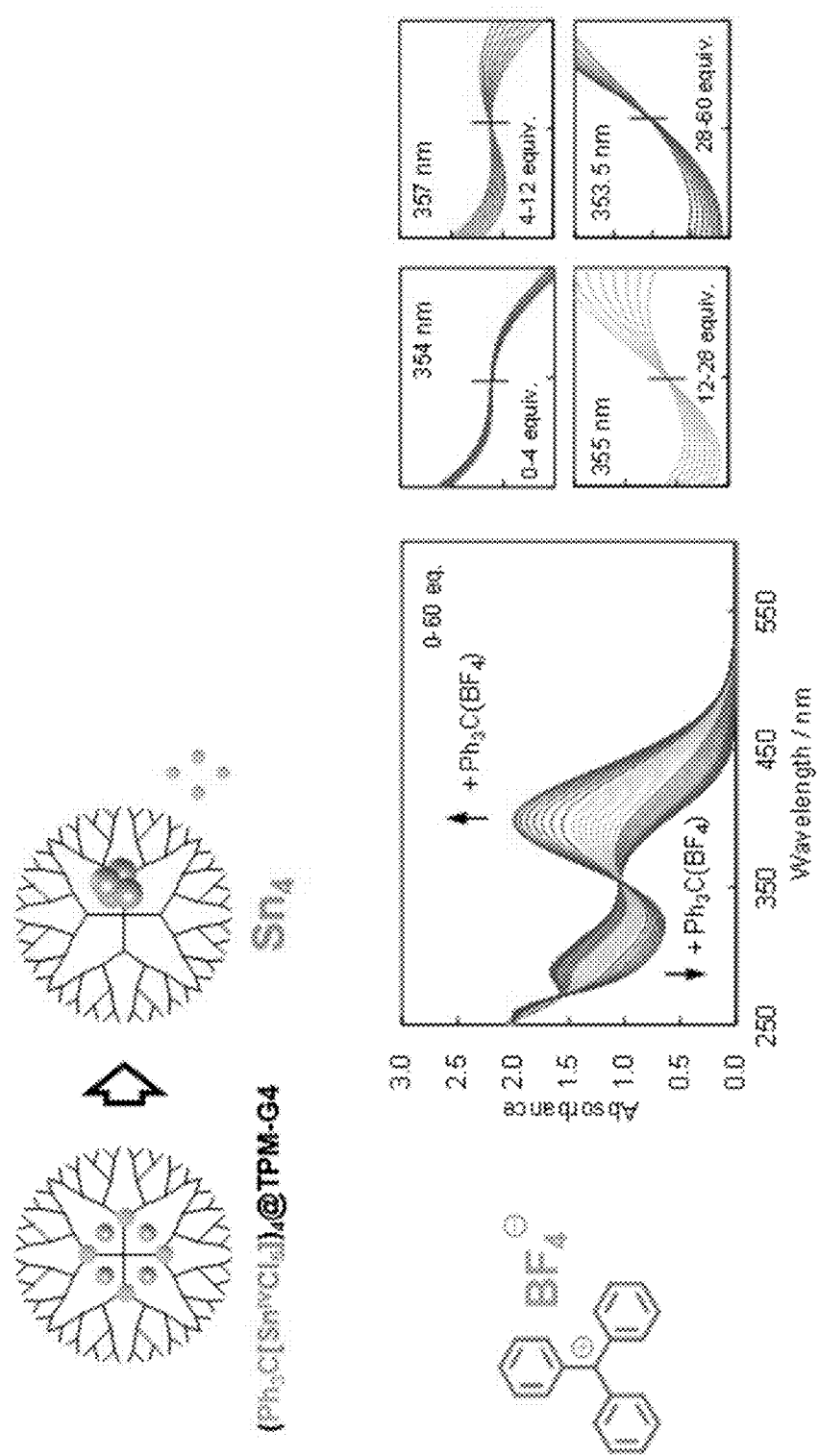
FIG. 18 is graphs showing the change of the ultraviolet-visible absorption spectrum when tetrafluoroborate of triphenylmethylium cation ($Ph_3C^+$) are dripped in the solution of TPM-G1.

FIG. 18 shows the titration by the ultraviolet-visible absorption spectrum when tetrafluoroborate of triphenylmethylium cation ($Ph_3C^+$) was assembled in the TPM-G4 dendrimer. The solvent is DOX (dioxane)/THF (tetrahydrofuran)=20:1, the density of TPM-G4 is 3 μM, and the temperature is 20° C. The isosbestic points were confirmed separately in the four layers.

The results indicate that not just the metal salt but also the organic cation can be precisely assembled in the dendrimer.

Figure 19:
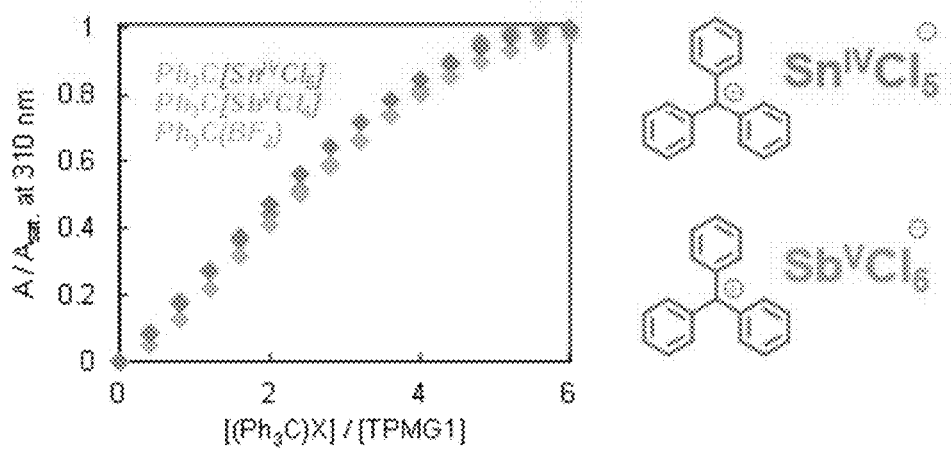
FIG. 19 is graphs obtained by plotting A/Asat. at 310 nm to the density ratio: metal salt/TPM-G1 when the salt of triphenylmethylium cation and chloride and bromide (lower graphs) are dripped in the solution of TPM-G1 for each of tetrafluoroborate, pentachlorotinate, and hexachloroantimonate (upper graph) of triphenylmethylium cation, tin, and antimony.
Figure 19:
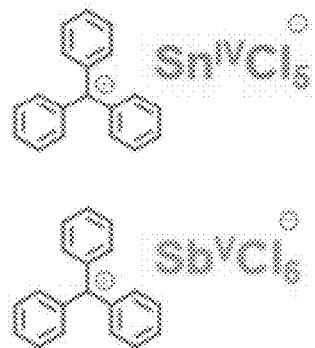
Figure 19:
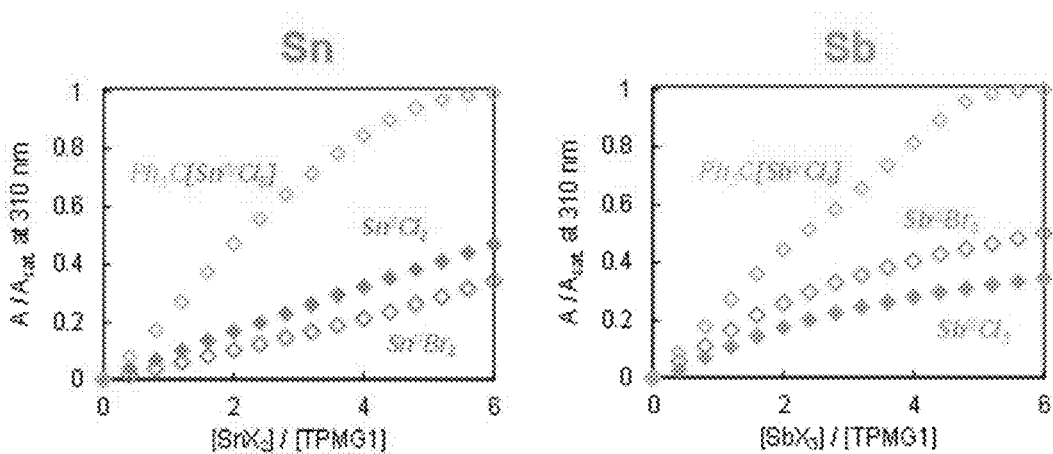

FIG. 19 shows, in the upper part, the plots for comparing the coordination trend of tetrafluoroborate, pentachlorotinate, hexachloroantimonate of triphenylmethylium cation ($BF_4^-$, $[Sn^{IV}Cl_5]^-$, $[Sb^VCl_6]^-$) using the model compound TPM-G1. The solvent is DCM (dichloromethane)/AN (acetonitrile)=1:1, the density of TPM-G1 is 30 μM, and the temperature is 20° C. By using the coordination trend of the organic cation, the assembling of metal as the counter anion is possible.

The plots indicate that the coordination trend of triphenylmethylium cation does not very much depend on the counter anion. On the other hand, FIG. 19 shows, in the lower part, the plots for comparing the coordination trend of the salt and chloride and bromide of the triphenylmethylium cation regarding each of tin and antimony. Thus, even with the same element, the coordination trend in the metal assembling can be varied.
(Assembling by Proton)

By using the coordination trend of, not the metal salt itself, but the proton, the assembling of metal as the counter anion was attempted.

Figure 20:
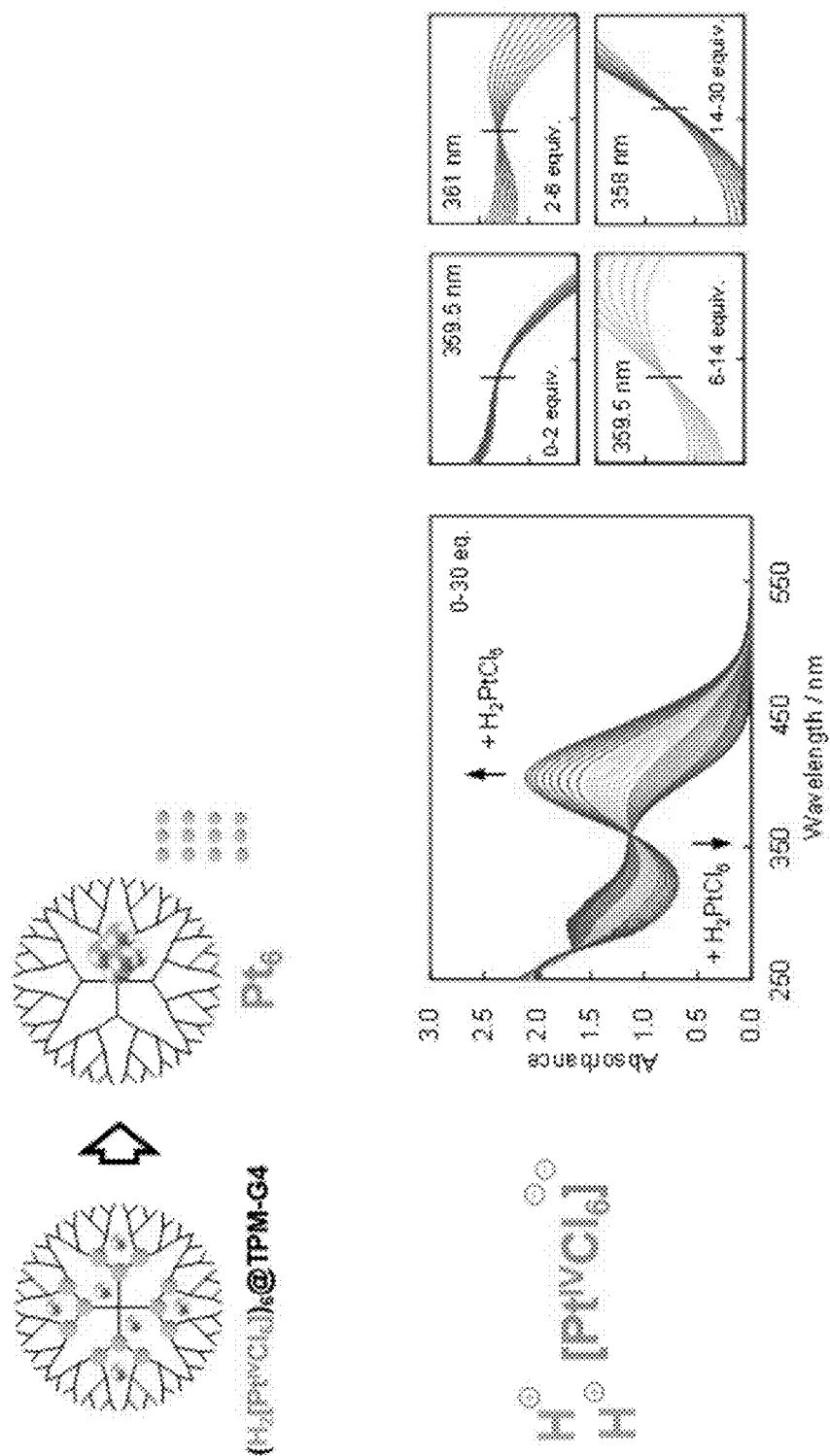
FIG. 20 is graphs showing the change of the ultraviolet-visible absorption spectrum when hexachloroplatinate is dripped in the solution of TPM-G1.

FIG. 20 shows the titration by the ultraviolet-visible absorption spectrum when hexachloroplatinate was assembled in the TPM-G4 dendrimer. The solvent is DOX (dioxane)/AN (acetonitrile)=1:1, the density of TPM-G4 is 3 μM, and the temperature is 20° C. The isosbestic points were confirmed separately in the four layers.

The results indicate that not just the metal salt but also the proton can be precisely assembled in the dendrimer.

Figure 21:
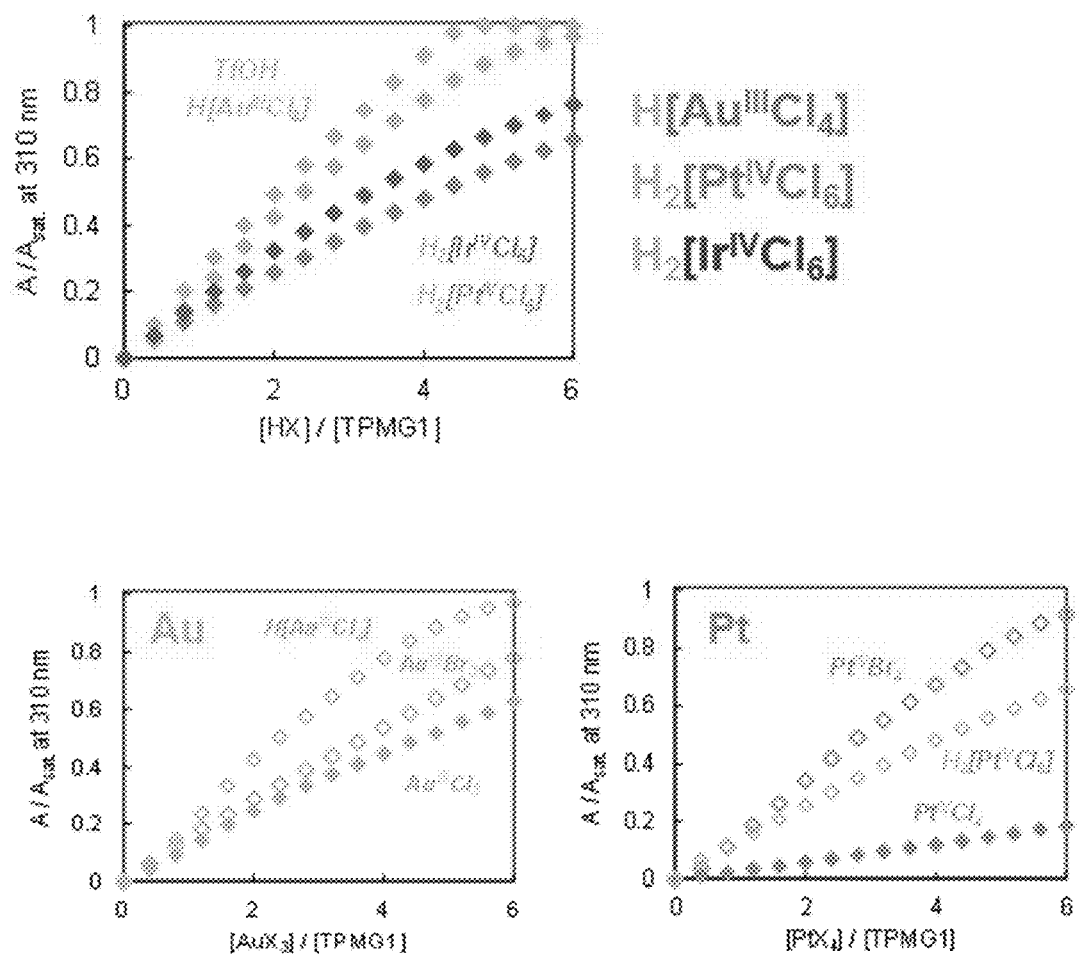
FIG. 21 is graphs obtained by plotting A/Asat. at 310 nm to the density ratio: metal salt/TPM-G1 when the proton compound and the chloride and bromide (lower graphs) are dripped in the solution of TPM-G1 for each of trifluoromethane sulfonate, tetrachloroaurate, hexachloroplatinate, hexachloroiridate (upper graph), gold, and platinum.

FIG. 21 shows, in the upper part, the plots for comparing the coordination trend of trifluoromethane sulfonate, tetrachloroaurate, tetrachloroplatinate, and hexachloroiridate (TfOH, $H[Au^{III}Cl_4]$, $H_2[Pt^{IV}Cl_6]$, $H_2[Ir^{IV}Cl_6]$) using the model compound TPM-G1. The solvent is DCM (dichloromethane)/AN (acetonitrile)=1:1, the density of TPM-G1 is 30 μM, and the temperature is 20° C.

From the plots, it is supposed that the coordination trend of the proton changes depending on the pKa of the acid. By using the coordination trend of the proton in this manner, the assembling of metal as the counter anion is possible.

On the other hand, FIG. 21 shows, in the lower part, the plots for comparing the coordination trend of the proton compound and the chloride and bromide for each of gold and platinum. Thus, even with the same element, the coordination trend in the metal assembling can be varied.

In addition, in a polyvalent metal complex anion ($[Pt^{IV}Cl_6]^{2-}$, $[Ir^{IV}Cl_6]^{2-}$), the number of protons is different for the metal; therefore, the control with a special number of assemblies can be performed.

Reference Example 3

Control of Coordination Trend by Oxidation Number of Metal Salt

Figure 22:
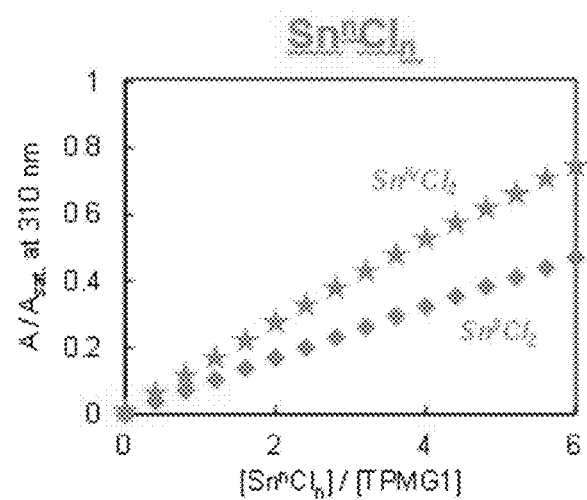
FIG. 22 is a graph obtained by measuring the change of the ultraviolet-visible absorption spectrum when tin chloride with the oxidation number changed to +II valent and +IV valent is dripped in the solution of TPM-G1 and plotting the absorbance A/Asat. at 310 nm to the density ratio: metal salt/TPM-G1.

The coordination trend can be controlled also by changing the oxidation number of metal salt. FIG. 22 shows the plots of the change of the coordination trend when the oxidation number of tin chloride was changed to +II valent and +IV valent using the model compound TPM-G1. The solvent is DCM (dichloromethane)/AN (acetonitrile)=1:1, the density of TPM-G1 is 30 μM, and the temperature is 20° C. In order to exactly examine the effect of the oxidation number, the counter anion of the metal is the same in the comparison.

The results indicate that the coordination trend increases in the order of $Sn^{IV}Cl_4 > Sn^{II}Cl_2$. The coordination trend was controlled successfully by changing the oxidation number.

Figure 23:
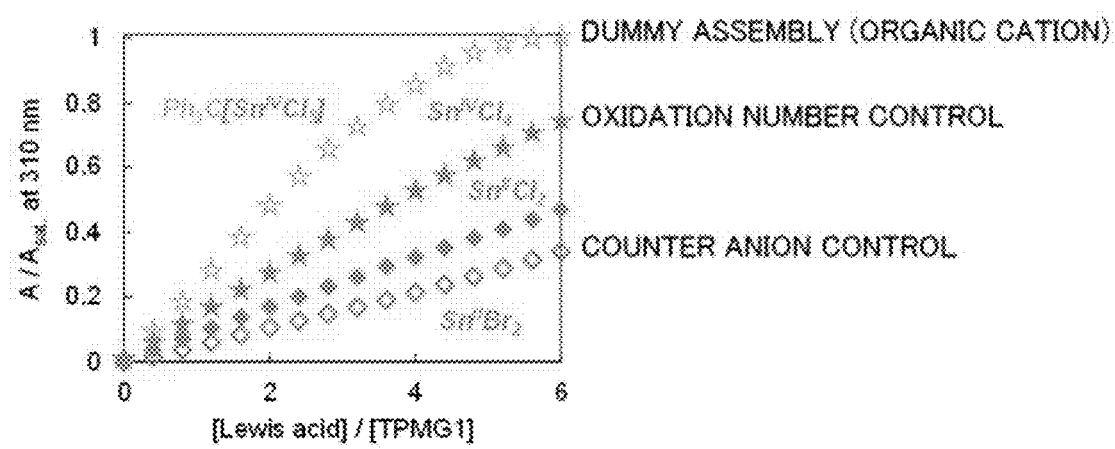
FIG. 23 is a graph obtained by measuring the change of the ultraviolet-visible absorption spectrum when the counter anion is changed, the oxidation number is changed, or the halogenated tin introduced as the counter complex anion of triphenylmethylium cation that is the organic cation is dripped into the solution of TPM-G1, and plotting the absorbance A/Asat. at 310 nm to the density ratio: metal salt/TPM-G1.

From the above Reference examples 1 to 3, for example in the case of tin as the metal species, the coordination trend can be variously controlled by changing the counter anion, changing the oxidation number, using the dummy assembling method, or the like as shown in FIG. 23.

Example 5

Figure 24:
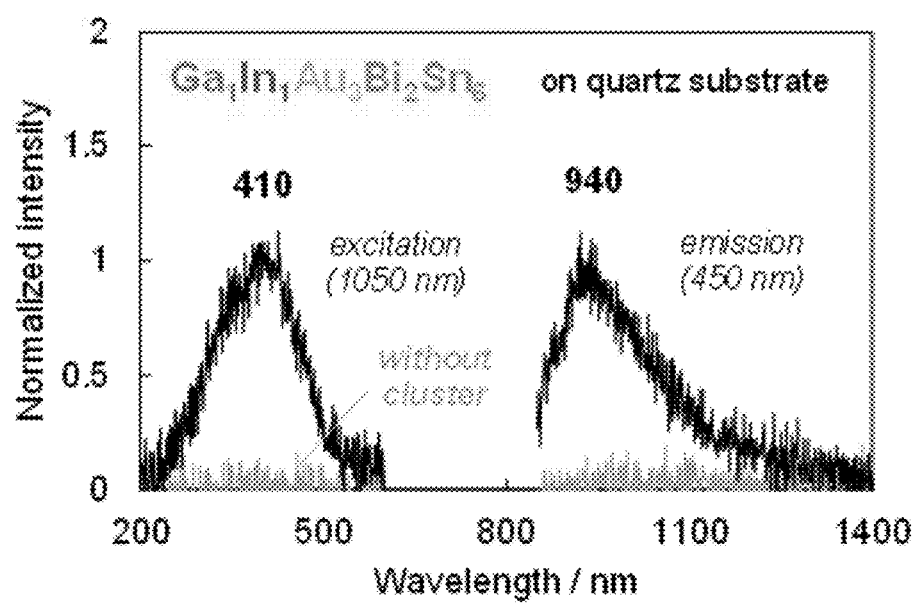
FIG. 24 shows the UV-VIS excitation spectrum and the NIR light-emission spectrum of a sample in which a 5-element cluster that is reduced and synthesized in the solution is casted on an optically transparent quartz substrate and dried. The 5-element cluster sample has a light-emission spectrum in a near-infrared area around 940 nm, and judging from the UV-VIS absorption (not shown) and the excitation spectrum, the excitation wavelength of the 5-element cluster sample is near 410 nm. It also shows that light is not emitted just by the dendrimer and the reducing agent.

Five-element cluster (containing dendrimer and reducing agent) that is educed and synthesized in the solution using $GaCl_3$, $InBr_3$, $AuCl_3$, $BiCl_3$, and $SnBr_2$ was casted on a quartz substrate and dried, and the resulting product was used as a sample. Using this sample, the optical characteristics (absorption and light-emitting characteristics) were examined. The UV-VIS excitation spectrum and the NIR light-emission spectrum of the sample are shown in FIG. 24 (Integration 0.1 s/nm, Average 30). The five-element cluster sample had light emission at about 940 nm in a near-infrared region. It has been confirmed that this light emission never occurs with the dendrimer and the reducing agent only. In addition, judging from the UV-VIS absorption and the excitation spectrum, the cluster absorption was at about 410 nm.

The invention claimed is:

1. A multiple-metal salt assembly of dendrimer, wherein four or more types of multiple-metal salt compounds with multiple metal species are assembled for each of parts with different environments in a dendrimer whose core is a group expressed by a following Formula (I):

[Chem. 1]

$$-(X)_nC(Ph)_{4-n}- \qquad (I)$$

(wherein n number of Xs independently represent a divalent group corresponding to a residue of a six-membered ring aromatic heterocyclic compound including, as a hetero atom, at least one selected from nitrogen, phosphorus, and arsenic, a derivative thereof, or a benzene derivative including an electron-donating functional group, Ph represents a phenylene group, and n represents an integer of 1 to 3.

2. The multiple-metal salt assembly of dendrimer according to claim 1, wherein four to eight types of multiple-metal salt compounds with multiple metal species are assembled.

3. The multiple-metal salt assembly of dendrimer according to claim 1, wherein the dendrimer includes, as the part with the different environment, an imine part that forms a complex with the multiple-metal salt compound.

4. The multiple-metal salt assembly of dendrimer according to claim 3, wherein the dendrimer is phenylazomethine dendrimer.

5. The multiple-metal salt assembly of dendrimer according to claim 1, wherein the multiple-metal salt compound is a multiple-metal salt that is directly coordinated to the part with the different environment in the dendrimer or a compound in which proton or an organic cation for which the multiple-metal salt is a counter anion is coordinated to the part and assembled.

6. A method for producing a multiple-metal salt assembly of dendrimer in which four or more types of multiple-metal salt compounds with multiple metal species are assembled for each of parts with different environments, the method comprising the steps of:
preparing a solution containing dendrimer whose core is a group expressed by a following Formula (I):

[Chem. 2]

$$—(X)_nC(Ph)_{4-n}— \qquad (I)$$

(in which n number of Xs independently represent a divalent group corresponding to a residue of a six-membered ring aromatic heterocyclic compound including, as a hetero atom, at least one selected from nitrogen, phosphorus, and arsenic, a derivative thereof, or a benzene derivative including an electron-donating functional group, Ph represents a phenylene group, and n represents an integer of 1 to 3); and
mixing the solution with the four or more types of multiple-metal salt compounds with different interaction strength for each of the parts with the different environments in the dendrimer, so as to obtain the multiple-metal salt assembly of dendrimer in which the four or more types of multiple-metal salt compounds are assembled for each of the parts with the different environments.

7. The method for producing a multiple-metal salt assembly of dendrimer according to claim 6, wherein four to eight types of multiple-metal salt compounds with multiple metal species are assembled for each of parts with different environments.

8. The method for producing a multiple-metal salt assembly of dendrimer according to claim 6, wherein the multiple-metal salt compounds are mixed by an amount corresponding to an equivalent for one of the parts with the different environments where the compounds are assembled or a total equivalent for two or more of the parts with the different environments where the compounds are assembled.

9. The method for producing a multiple-metal salt assembly of dendrimer according to claim 6, wherein when one type of the multiple-metal salt compounds is mixed and then another type of the multiple-metal salt compounds is mixed, an isosbestic point in an ultraviolet-visible absorption spectrum of the solution changes.

10. The method for producing a multiple-metal salt assembly of dendrimer according to claim 6, wherein the four or more types of multiple-metal salt compounds are assembled to each of the parts with the different environments in the same order when mixed in the solution containing the dendrimer.

11. The method for producing a multiple-metal salt assembly of dendrimer according to claim 6, wherein the multiple-metal salt compound is a multiple-metal salt that is directly coordinated to the part with the different environment in the dendrimer or a compound in which proton or an organic cation for which the multiple-metal salt is a counter anion is coordinated to the part and assembled.

12. The method for producing a multiple-metal salt assembly of dendrimer according to claim 6, wherein the dendrimer includes, as the part with the different environment, an imine part that forms a complex with the multiple-metal salt compound.

13. The method for producing a multiple-metal salt assembly of dendrimer according to claim 12, wherein the dendrimer is phenylazomethine dendrimer.

14. A method for producing subnano metal particles including four or more types of multiple metals, wherein the multiple-metal salt assembly of dendrimer according to claim 1 is reduced.

15. The multiple-metal salt assembly of dendrimer according to claim 3, wherein X in the Formula (I) is a divalent group corresponding to a residue of a six-membered ring aromatic heterocyclic compound including, as a hetero atom, at least one selected from nitrogen, phosphorus, and arsenic, or a derivative thereof.

16. The multiple-metal salt assembly of dendrimer according to claim 15, wherein X in the Formula (I) is a divalent group corresponding to a residue of a six-membered ring aromatic heterocyclic compound including nitrogen as a hetero atom.

17. The multiple-metal salt assembly of dendrimer according to claim 16, wherein five to eight types of multiple-metal salt compounds with multiple metal species are assembled.

18. The multiple-metal salt assembly of dendrimer according to claim 4, wherein X in the Formula (I) is a divalent group corresponding to a residue of a six-membered ring aromatic heterocyclic compound including, as a hetero atom, at least one selected from nitrogen, phosphorus, and arsenic, or a derivative thereof.

19. The multiple-metal salt assembly of dendrimer according to claim 18, wherein X in the Formula (I) is a divalent group corresponding to a residue of a six-membered ring aromatic heterocyclic compound including nitrogen as a hetero atom.

20. The multiple-metal salt assembly of dendrimer according to claim 19, wherein five to eight types of multiple-metal salt compounds with multiple metal species are assembled.

* * * * *